United States Patent
Muramatsu et al.

(10) Patent No.: US 10,894,955 B2
(45) Date of Patent: Jan. 19, 2021

(54) MUTANT DECARBONYLASE GENE, RECOMBINANT MICROORGANISM COMPRISING THE MUTANT DECARBONYLASE GENE, AND METHOD FOR PRODUCING ALKANE

(71) Applicant: TOYOTA JIDOSHA KABUSHIKI KAISHA, Toyota (JP)

(72) Inventors: Masayoshi Muramatsu, Miyoshi (JP); Shusei Obata, Nagoya (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 0 days.

(21) Appl. No.: 16/777,128

(22) Filed: Jan. 30, 2020

(65) Prior Publication Data
US 2020/0248164 A1 Aug. 6, 2020

(30) Foreign Application Priority Data

Feb. 1, 2019 (JP) ................................ 2019-017251

(51) Int. Cl.
*C12N 15/63* (2006.01)
*C12N 9/88* (2006.01)
*C12P 5/02* (2006.01)
*C12N 1/20* (2006.01)

(52) U.S. Cl.
CPC ................. *C12N 9/88* (2013.01); *C12N 1/20* (2013.01); *C12P 5/02* (2013.01); *C12Y 401/99005* (2013.01); *C12N 2510/02* (2013.01)

(58) Field of Classification Search
CPC ..................................................... C12N 9/16
USPC ........................................................ 435/167
See application file for complete search history.

(56) References Cited

U.S. PATENT DOCUMENTS

| 8,268,599 B2 | 9/2012 | Schirmer et al. |
| 8,846,371 B2 | 9/2014 | Schirmer et al. |
| 2014/0186915 A1 | 7/2014 | Mori |

FOREIGN PATENT DOCUMENTS

| JP | 2011-522525 A | 8/2011 |
| WO | 2013/024527 A1 | 2/2013 |

OTHER PUBLICATIONS

Hayashi et al. 2015, vol. 10, No. 4, pp. 1-14 (Year: 2015).*
Andreas Schirmer et al., "Microbial Biosynthesis of Alkanes", Science, vol. 329, pp. 559-562, 2010, 5 pages.
Nicolaas A Buijs et al., "Long-chain Alkane Production by the Yeast *Saccharomyces cerevisiae*", Biotechnology and Bioengineering, Jun. 2015, vol. 112, No. 6, pp. 1275-1279.
Carl Andre et al, "Fusing catalase to an alkane-producing enzyme maintains enzymatic activity by converting the inhibitory byproduct $H_2O_2$ to the cosubstrate $O_2$", Proceedings of the National Academy of Sciences of the United States of America, 2013, pp. 3191-3196.
AE Kyung Park et al. "Crystal structures of aldehyde deformylating oxygenase from *Limnothrix* sp. KNUA012 and *Oscillatoria* sp. KNUA011", Biochemical and Biophysical Research Communications, 477, 2016, 395-400, 6 pages.
Chenjun Jia et al, "Structural insights into the catalytic mechanism of aldehyde-deformylating oxygenases", Protein Cell, 2015, vol. 6, pp. 55-67.

* cited by examiner

*Primary Examiner* — Tekchand Saidha
(74) *Attorney, Agent, or Firm* — Sughrue Mion, PLLC

(57) ABSTRACT

The present disclosure is intended to identify a substitution mutation that improves enzyme activity of a decarbonylase. An amino acid corresponding to an amino acid 90, 107, 163, or 171 in SEQ ID NO: 2 is to be substituted with an amino acid exhibiting a higher degree of hydrophobicity.

11 Claims, 2 Drawing Sheets

Specification includes a Sequence Listing.

Fig. 1

```
1    MQQLTDQSKELDFKSETYKDAYSRINAIVIEGEQEAHENYITLAQLLPESHDELIRLSKM    60
              ①                                    ②
                                               90th
                                                ↓
61   ESRHKKGFEACGRNLAVTPDLQFAKEFFSGLHQNFQTAAAEGKVVTCLLIQSLIIECFAI   120
              ③                                         ④        ⑤
                                            163rd    171st
                                              ↓        ↓
121  AAYNIYIPVADDEARKITEGVVKEEYSHLNEGEVWLKEHFAESKAELELANRQNLPIVWK   180
              ⑥                    ⑦                ⑧
181  MLNQVEGDAHTMAMEKDALVEDEMIQYGEALSNIGFSTRDIMRLSAYGLIGA           232
              ⑨                              ⑩
```

MUTANT DECARBONYLASE GENE, RECOMBINANT MICROORGANISM COMPRISING THE MUTANT DECARBONYLASE GENE, AND METHOD FOR PRODUCING ALKANE

CROSS REFERENCE TO RELATED APPLICATIONS

The present application claims priority from Japanese patent application JP 2019-017251 filed on Feb. 1, 2019, the content of which is hereby incorporated by reference into this application.

BACKGROUND

Technical Field

The present disclosure relates to a mutant decarbonylase gene encoding a decarbonylase mutant having a substitution mutation of an amino acid, a recombinant microorganism having such mutant decarbonylase gene, and a method for producing alkane.

Background Art

Alkane is contained in petroleum, it is purified by fractional distillation, and it is used for a wide variety of applications. In addition, alkane is extensively used as a raw material in chemical industry, and it is also a main component of a diesel fuel obtained from petroleum. In recent years, a technique of coexpressing an acyl ACP reductase gene derived from blue-green algae and a decarbonylase gene in E. coli and producing alkane, which is a light oil component, via fermentation has been developed (U.S. Pat. No. 8,846,371).

A decarbonylase, which is a key enzyme in alkane synthesis, is reported to need ferredoxin and ferredoxin reductase to exert its activity (Science, Vol. 329, pp. 559-562, 2010; and WO 2013/024527). When synthesizing alkane with Saccharomyces cerevisae, it is reported that the E. coli-derived ferredoxin gene and the ferredoxin reductase gene are required to be expressed in addition to the decarbonylase gene (Biotechnology Bioengineering, Vol. 112, No. 6, pp. 1275-1279, 2015). According to Biotechnology Bioengineering, Vol. 112, No. 6, pp. 1275-1279, 2015, the amount of alkane produced is approximately 3 µg/g of dry cells. In this case, Saccharomyces cerevisae has an O.D. 600 of approximately 20 at full growth, and the dry cell weight is approximately 4 g of dry cells/l. On the basis thereof, the amount of production is understood to be as low as approximately 12 µg/l according to the method disclosed in Biotechnology Bioengineering, Vol. 112, No. 6, pp. 1275-1279, 2015.

It has been pointed out that decarbonylase activity is lowered or lost by hydrogen peroxide produced at the time of the reaction (Proceedings of the National Academy of Sciences of the United States of America, 110, 8, 2013, 3191-3196). According to Proceedings of the National Academy of Sciences of the United States of America, 110, 8, 2013, 3191-3196, the activity lowered or lost due to hydrogen peroxide can be improved in the form of a fusion protein of a decarbonylase and a catalase. Also, a decarbonylase has been subjected to crystalline structure analysis, and information concerning the enzyme reaction mechanism and the amino acid residues involved in the reaction has been elucidated (Biochemical and Biophysical Research Communications, 477, 2016, 395-400; and Protein Cell 6, 1, 2015, 55-67).

SUMMARY

A conventional decarbonylase was insufficient in terms of enzyme activity. Under the above circumstances, accordingly, the present disclosure is intended to identify a substitution mutation that improves enzyme activity of a decarbonylase and to provide a mutant decarbonylase gene encoding a decarbonylase comprising such substitution mutation, a recombinant microorganism comprising such mutant decarbonylase gene, and a method for producing alkane.

We have conducted concentrated studies in order to overcome the problems indicated above. As a result, we discovered that enzyme activity could be improved to a significant extent by substitution of a particular amino acid residue of a decarbonylase, thereby leading to the completion of the present disclosure.

Specifically, the present disclosure includes the following.

(1) A mutant decarbonylase gene encoding a decarbonylase comprising at least one substitution mutation in the amino acid sequence as shown in SEQ ID NO: 2, wherein the mutation is selected from the group consisting of:

a substitution mutation of an amino acid corresponding to glycine 90 with an amino acid exhibiting a higher degree of hydrophobicity;

a substitution mutation of an amino acid corresponding to cysteine 107 with an amino acid exhibiting a higher degree of hydrophobicity;

a substitution mutation of an amino acid corresponding to serine 163 with an amino acid exhibiting a higher degree of hydrophobicity; and a substitution mutation of an amino acid corresponding to asparagine 171 with an amino acid exhibiting a higher degree of hydrophobicity.

(2) The mutant decarbonylase gene according to (1), wherein the amino acid exhibiting a higher degree of hydrophobicity is an amino acid selected from the group consisting of phenylalanine, leucine, valine, and isoleucine.

(3) The mutant decarbonylase gene according to (1), wherein the amino acid corresponding to glycine 90 is substituted with valine.

(4) The mutant decarbonylase gene according to (1), wherein the amino acid corresponding to cysteine 107 is substituted with valine.

(5) The mutant decarbonylase gene according to (1), wherein the amino acid corresponding to serine 163 is substituted with valine.

(6) The mutant decarbonylase gene according to (1), wherein the amino acid corresponding to asparagine 171 is substituted with leucine.

(7) A recombinant microorganism comprising the mutant decarbonylase gene according to any of (1) to (6) introduced into a host microorganism.

(8) The recombinant microorganism according to (7), wherein the host microorganism is a bacterium of the genus Escherichia or Klebsiella.

(9) A method for producing alkane comprising culturing the recombinant microorganism according to (7) or (8).

(10) The method for producing alkane according to (9), which further comprises recovering alkane from a medium in which the recombinant microorganism is cultured.

(11) The method for producing alkane according to (9), which further comprises recovering alkane from a medium in which the recombinant microorganism is cultured and purifying the recovered alkane.

(12) The method for producing alkane according to (9), which further comprises producing alkane having 9 to 20 carbon atoms.

The mutant decarbonylase gene according to the present disclosure encodes a protein comprising decarbonylase activity superior to that of a wild-type decarbonylase without a mutation. With the use of the mutant decarbonylase gene according to the present disclosure, accordingly, a recombinant microorganism excellent in the alkane-synthesizing capacity can be obtained. In addition, alkane productivity in an alkane synthesis system that involves the use of a recombinant microorganism into which the mutant decarbonylase gene according to the present disclosure has been introduced can be improved to a significant extent, and the cost incurred in alkane production can be reduced to a significant extent.

BRIEF DESCRIPTION OF THE DRAWINGS

FIG. 1 schematically shows 10 α helix structures (Helix 1 to Helix 10, underlined) and amino acid residues to be substituted (indicated by arrows) in the amino acid sequence of the decarbonylase derived from the *N. punctiforme* PCC 73102 strain (SEQ ID NO: 2).

DETAILED DESCRIPTION

Figure 2:
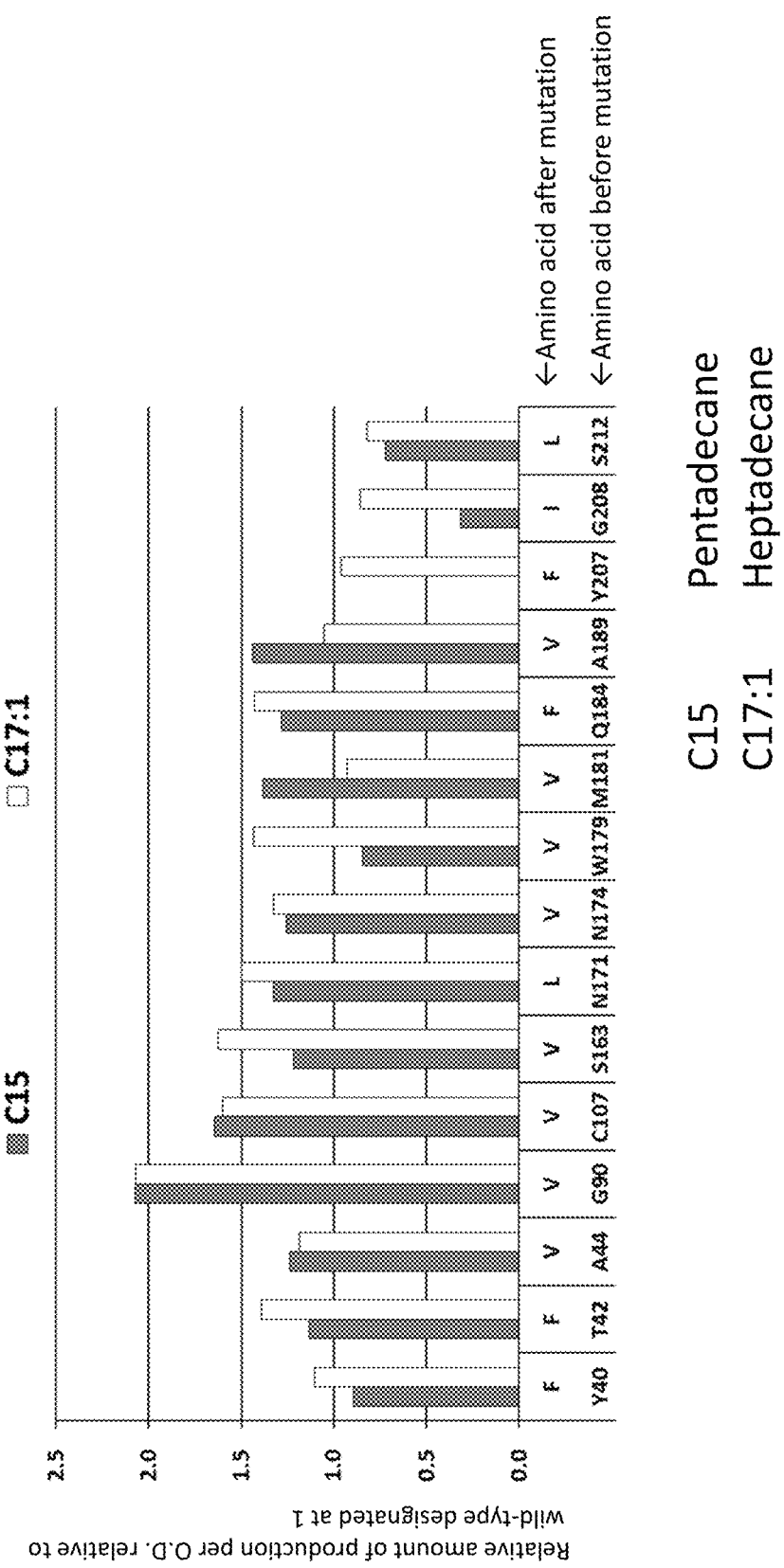
FIG. 2 shows a characteristic diagram demonstrating the results of measuring the amount of hydrocarbons (pentadecane and heptadecane) produced by a transformant resulting from introduction of a mutant decarbonylase gene.

Hereafter, the present disclosure is described in greater detail with reference to the figures and the examples.

The mutant decarbonylase gene according to the present disclosure (hereafter, simply referred to as "the mutant decarbonylase gene") encodes a decarbonylase mutant prepared by introducing a given substitution mutation into a wild-type decarbonylase. In particular, the decarbonylase mutant comprising a substitution mutation introduced thereinto exhibits decarbonylase activity superior to that of a decarbonylase before introduction of the mutation (e.g., a wild-type decarbonylase). The term "decarbonylase activity" used herein refers to activity of decarbonylating an aldehyde compound serving as a substrate to produce a hydrocarbon. Thus, decarbonylase activity can be evaluated based on the amount of hydrocarbons produced.

The term "a substitution mutation" used herein refers to a mutation that substitutes a given amino acid residue included in an α helix constituting a decarbonylase with another amino acid, and an amino acid residue to be substituted is selected from among amino acid residues that may strengthen a hydrophobic bond between the α helix structures. More specifically, amino acid residues to be substituted are selected from among amino acid residues exhibiting a lower degree of hydrophobicity among amino acid residues associated with a hydrophobic bond between the α helix structures.

By substituting the target amino acid residue with an amino acid residue with a higher degree of hydrophobicity, the resulting decarbonylase activity becomes superior to the decarbonylase activity before the mutation. An amino acid residue after the mutation can be arbitrarily selected from among amino acid residues exhibiting a higher degree of hydrophobicity than the amino acid to be substituted.

Concerning the degree of hydrophobicity, the hydropathy index (also referred to as "the hydrophobicity scale") described in, for example, Kyte J. & Doolittle R F, 1982, J. Mol. Biol., 157: 105-132 can be employed. A degree of hydrophobicity is not limited to the degree of hydrophobicity defined by Kyte J. & Doolittle R F. For example, the degree of hydrophobicity disclosed in Hopp T P, Woods K R, 1983, Mol. Immunol., 20 (4): 483-489 or the degree of hydrophobicity disclosed in Engelman D M, Steitz T A, Goldman A, 1986, Annu. Rev. Biophys. Biophys. Chem., 15: 321-353 can be adequately employed.

Table 1 shows the degree of hydrophobicity defined by Kyte J. & Doolittle R F concerning 20 amino acid species.

TABLE 1

| Amino acid | Degree of hydrophobicity (Kyte-Doolittle) |
|---|---|
| R | −4.5 |
| K | −3.9 |
| D | −3.5 |
| E | −3.5 |
| N | −3.5 |
| Q | −3.5 |
| H | −3.2 |
| P | −1.6 |
| Y | −1.3 |
| W | −0.9 |
| S | −0.8 |
| T | −0.7 |
| G | −0.4 |
| A | 1.8 |
| M | 1.9 |
| C | 2.5 |
| F | 2.8 |
| L | 3.8 |
| V | 4.2 |
| I | 4.5 |

Specifically, an amino acid exhibiting a higher degree of hydrophobicity can be selected as the amino acid residue after the mutation on the basis of Table 1. In particular, the amino acid residue after the mutation may be selected from the group consisting of phenylalanine (F), leucine (L), valine (V), and isoleucine (I). By substituting an amino acid residue of interest with an amino acid selected from the group consisting of phenylalanine (F), leucine (L), valine (V), and isoleucine (I), a hydrophobic bond between the α helix structures can be further strengthened, and excellent decarbonylase activity can be achieved.

Hereafter, an amino acid residue to be substituted is described based on the amino acid sequence of a wild-type decarbonylase. For example, SEQ ID NO: 2 shows the amino acid sequence of the wild-type decarbonylase encoded by the decarbonylase gene derived from the *N. punctiforme* PCC 73102 strain. SEQ ID NO: 1 shows the nucleotide sequence of the coding region of the decarbonylase gene derived from the *N. punctiforme* PCC 73102 strain.

An amino acid residue to be substituted is at least 1 amino acid residue selected from the group consisting of glycine 90, cysteine 107, serine 163, and asparagine 171 in the amino acid sequence as shown in SEQ ID NO: 2. Such amino acid residues to be substituted are positioned in the α helix structures constituting a decarbonylase.

The decarbonylase derived from the *N. punctiforme* PCC 73102 strain is found to comprise 10 α helices as a result of the structural analysis based on the amino acid sequence thereof. Such 10 α helices are referred to as Helix 1 to Helix 10 sequentially from the N terminus. FIG. 1 shows the amino acid sequence of the decarbonylase derived from the *N. punctiforme* PCC 73102 strain (SEQ ID NO: 2) with numbering the 10 α helix structures (i.e., Helix 1 to Helix 10, underlined, the numbers are each in a circle). In FIG. 1, the amino acid residues to be substituted are indicated by arrows.

As shown in FIG. 1, amino acid residues to be substituted are positioned in Helix 3, Helix 4, and Helix 8. Glycine 90 is positioned in Helix 3, and this amino acid residue is highly likely to form a hydrophobic bond with isoleucine 177 positioned in Helix 8 on the basis of the results of conformational analysis. Cysteine 107 is positioned in Helix 4, and this amino acid residue is highly likely to form a hydrophobic bond with leucine 43 positioned in Helix 1, leucine 46 positioned in Helix 1, phenylalanine 95 positioned in Helix 3, alanine 98 positioned in Helix 3, and alanine 99 positioned in Helix 3 on the basis of the results of conformational analysis. Serine 163 is positioned in Helix 8, and this amino acid residue is highly likely to form a hydrophobic bond with valine 105 positioned in Helix 4 and leucine 156 positioned in Helix 7. Asparagine 171 is positioned in Helix 8, and this amino acid residue is highly likely to form a hydrophobic bond with leucine 109 positioned in Helix 4, tyrosine 207 positioned in Helix 9, leucine 224 positioned in Helix 10, and serine 225 positioned in Helix 10.

For example, glycine 90 of the decarbonylase derived from the *N. punctiforme* PCC 73102 strain comprising the amino acid sequence as shown in SEQ ID NO: 2 may be substituted with an amino acid residue exhibiting a higher degree of hydrophobicity, so that a hydrophobic bond between Helix 3 and Helix 8 can be strengthened, and excellent decarbonylase activity can be achieved. In some other embodiments, glycine 90 may be substituted with an amino acid selected from the group consisting of phenylalanine (F), leucine (L), valine (V), and isoleucine (I). In some other embodiments, glycine 90 may be substituted with valine (V).

Also, cysteine 107 of the decarbonylase derived from the *N. punctiforme* PCC 73102 strain comprising the amino acid sequence as shown in SEQ ID NO: 2 may be substituted with an amino acid residue exhibiting a higher degree of hydrophobicity, so that a hydrophobic bond between Helix 4 and Helix 1 and/or Helix 3 can be strengthened, and excellent decarbonylase activity can be achieved. In some other embodiments, cysteine 107 may be substituted with an amino acid selected from the group consisting of phenylalanine (F), leucine (L), valine (V), and isoleucine (I). In some other embodiments, cysteine 107 may be substituted with valine (V).

Further, serine 163 of the decarbonylase derived from the *N. punctiforme* PCC 73102 strain comprising the amino acid sequence as shown in SEQ ID NO: 2 may be substituted with an amino acid residue exhibiting a higher degree of hydrophobicity, so that a hydrophobic bond between Helix 8 and Helix 4 and/or Helix 7 can be strengthened, and excellent decarbonylase activity can be achieved. In some other embodiments, serine 163 may be substituted with an amino acid selected from the group consisting of phenylalanine (F), leucine (L), valine (V), and isoleucine (I). In some other embodiments, serine 163 may be substituted with valine (V).

Furthermore, asparagine 171 of the decarbonylase derived from the *N. punctiforme* PCC 73102 strain comprising the amino acid sequence as shown in SEQ ID NO: 2 may be substituted with an amino acid residue exhibiting a higher degree of hydrophobicity, so that a hydrophobic bond between Helix 8 and Helix 4, Helix 9, and/or Helix 10 can be strengthened, and excellent decarbonylase activity can be achieved. In some other embodiments, asparagine 171 may be substituted with an amino acid selected from the group consisting of phenylalanine (F), leucine (L), valine (V), and isoleucine (I). In some other embodiments, asparagine 171 may be substituted with leucine (L).

As described above, a decarbonylase mutant resulting from a substitution mutation of a given amino acid residue exhibits decarbonylase activity superior to that of a decarbonylase without such mutation (e.g., a wild-type decarbonylase). Accordingly, recombinant microorganisms that express decarbonylase mutants would have the hydrocarbon-producing capacity superior to that of microorganisms expressing, for example, a decarbonylase comprising the amino acid sequence as shown in SEQ ID NO: 2.

The mutant decarbonylase gene described above is not limited to the gene encoding the decarbonylase mutant resulting from introduction of the mutation into the amino acid sequence as shown in SEQ ID NO: 2. It may be a gene encoding the decarbonylase mutant resulting from introduction of the mutation into an amino acid sequence different from the amino acid sequence as shown in SEQ ID NO: 2. While a detailed description is provided below, for a decarbonylase comprising an amino acid sequence different from the amino acid sequence as shown in SEQ ID NO: 2, specific numerical values and amino acid types concerning the amino acid residues to be substituted are designated to be different from those concerning a decarbonylase comprising an amino acid sequence as shown in SEQ ID NO: 2.

An example of a decarbonylase comprising an amino acid sequence different from the amino acid sequence as shown in SEQ ID NO: 2 is a decarbonylase comprising an amino acid sequence having high similarity and/or identity to that of a wild-type decarbonylase encoded by the decarbonylase gene derived from the *N. punctiforme* PCC 73102 strain. A specific example thereof is a gene comprising an amino acid sequence having 50%, 60%, 70%, 80%, 85%, or 90% or higher identity to the amino acid sequence as shown in SEQ ID NO: 2 and encoding a protein having the decarbonylase activity as described above. Another specific example is a gene comprising an amino acid sequence having 80%, 85%, 90%, 95%, or 97% or higher similarity to the amino acid sequence as shown in SEQ ID NO: 2 and encoding a protein having the decarbonylase activity as described above.

The degree of sequence identity can be determined using the BLASTN or BLASTX Program equipped with the BLAST algorithm (at default settings). The degree of sequence identity is determined by subjecting a pair of amino acid sequences to pairwise alignment analysis, identifying completely identical amino acid residues, and calculating the percentage of all the amino acid residues subjected to comparison accounted for by such amino acid residues. The degree of sequence similarity is determined by subjecting a pair of amino acid sequences to pairwise alignment analysis, identifying completely identical amino acid residues and amino acid residues exhibiting similar functions, determining the total number of such amino acid residues, and calculating the percentage of all the amino acid residues subjected to comparison accounted for by the total number of such amino acid residues.

A decarbonylase comprising an amino acid sequence different from the amino acid sequence as shown in SEQ ID NO: 2 may be a protein comprising an amino acid sequence derived from the amino acid sequence as shown in SEQ ID NO: 2 by deletion, substitution, addition, or insertion of 1 to 50, 1 to 40, 1 to 30, or 1 to 20 amino acids and having decarbonylase activity.

A decarbonylase comprising an amino acid sequence different from the amino acid sequence as shown in SEQ ID NO: 2 may be a protein encoded by a gene hybridizing under stringent conditions to the full-length sequence or a partial sequence of a complementary strand of DNA comprising the nucleotide sequence as shown in SEQ ID NO: 1 and having decarbonylase activity. Under "stringent conditions," so-called specific hybrids are formed, but non-specific hybrids are not formed. For example, such conditions can be adequately determined with reference to Molecular Cloning: A Laboratory Manual (Third Edition). Specifically, the degree of stringency can be determined in accordance with the temperature and the salt concentration of a solution used for Southern hybridization and the temperature and the salt concentration of a solution used for the step of washing in Southern hybridization.

A method for preparing DNA comprising a nucleotide sequence encoding a decarbonylase comprising an amino acid sequence different from the amino acid sequence as shown in SEQ ID NO: 2 or DNA comprising a nucleotide sequence different from the nucleotide sequence as shown in SEQ ID NO: 1 is not particularly limited, and a known method can be adequately adopted. For example, given nucleotides can be substituted in accordance with a site-directed mutagenesis technique. Examples of site-directed mutagenesis techniques include a method of site-directed mutagenesis (i.e., the Kunkel method, T. Kunkel, T. A., Proc. Nati. Acad. Sci., U.S.A., 82, 488-492, 1985) and the Gapped duplex method. Alternatively, a mutation can be introduced with the use of, for example, a mutagenesis kit that adopts a site-directed mutagenesis technique (e.g., Mutan-K and Mutan-G, manufactured by TAKARA SHUZO CO., LTD.) or an LA PCR in vitro Mutagenesis series kit manufactured by TAKARA SHUZO CO., LTD.

Table 2 shows a list of microorganisms comprising genes each encoding a decarbonylase comprising an amino acid sequence having high similarity and/or identity to the wild-type decarbonylase encoded by the decarbonylase gene derived from the *N. punctiforme* PCC 73102 strain.

TABLE 2

| Alkane-synthesizing capacity | Organism | Similarity (%) | Identity (%) | Gene | GenBank accession No. |
|---|---|---|---|---|---|
| | *Nostoc* sp. KVJ20 | 99.5 | 95.2 | A4S05_30645 | ODH01054 |
| | *Anabaena cylindrica* PCC 7122 | 98.2 | 87.0 | Anacy_3389 | AFZ58792 |
| | *Anabaena azollae* 0708 | 98.7 | 86.6 | Aazo_3371 | ADI65029 |
| | *Nostoc* sp. PCC 7524 | 97.4 | 86.1 | Nos7524_4304 | AFY50063 |
| | *Calothrix* sp. PCC 7507 | 99.1 | 86.1 | Cal7507_5586 | AFY35912 |
| | *Anabaena* sp. Wa102 | 96.9 | 85.7 | AA650_00525 | ALB39141 |
| | *Cylindrospermum stagnale* PCC 7417 | 98.2 | 85.3 | Cylst_0697 | AFZ23025 |
| | *Fischerella* sp. NIES-3754 | 98.2 | 85.2 | FIS3754_06310 | BAU04742 |
| o | *Hapalosiphon welwitschii* IC-52-3 | 98.2 | 85.2 | none | AHH34192 |
| o | *Westiella intricate* HT-29-1 | 98.2 | 85.2 | none | AHH34193 |
| | *Gloeocapsa* sp. PCC 7428 | 97.4 | 84.9 | Glo7428_0150 | AFZ28764 |
| | *Anabaena* sp. 90 | 96.9 | 84.9 | ANA_C11210 | AFW93991 |
| | *Nostoc* sp. NIES-3756 | 96.5 | 83.9 | NOS3756_54760 | BAT56469 |
| | *Microcoleus* sp. PCC 7113 | 96.5 | 83.5 | Mic7113_4535 | AFZ20220 |
| | *Chroococcidiopsis thermalis* PCC 7203 | 97.4 | 82.6 | Chro_1554 | AFY87078 |
| | *Calothrix* sp. PCC 6303 | 97.4 | 82.6 | Cal6303_4369 | AFZ03276 |
| o | *Nostoc* sp. PCC 7120 (*Anabaena* sp. PCC 7120) | 97.8 | 82.6 | alr5283 | BAB76982 |
| | *Nostoc* sp. PCC 7107 | 95.6 | 82.2 | Nos7107_1028 | AFY41687 |
| | *Calothrix* sp. 336_3 | 97.4 | 81.8 | IJ00_07390 | AKG21145 |
| | *Nostoc punctiforme* PCC73102 | 97.4 | 81.3 | Npun_R1711 | ACC80382 |
| | *Crinalium epipsammum* PCC 9333 | 96.9 | 81.2 | Cri9333_4418 | AFZ15201 |
| | *Cyanothece* sp. PCC 8802 | 96.5 | 80.5 | none | Cyan8802_0468(KEGG)* |
| | *Cyanothece* sp. PCC 8801 | 96.5 | 80.5 | PCC8801_0455 | ACK64551 |
| | *Rivularia* sp. PCC 7116 | 97.4 | 80.5 | Riv7116_3790 | AFY56233 |
| | *Oscillatoria acuminata* PCC 6304 | 96.1 | 79.7 | Oscil6304_2075 | AFY81740 |
| | *Cyanothece* sp. ATCC 51142 | 96.1 | 77.9 | cce_0778 | ACB50129 |
| | *Arthrospira platensis* NIES-39 | 95.2 | 77.9 | NIES39_M01940 | BAI93031 |
| o | *Gloeobacter violaceus* PCC 7421 | 96.1 | 77.9 | gll3146 | BAC91087 |
| | *Oscillatoria nigro-viridis* PCC 7112 | 97.3 | 77.8 | Osc7112_0944 | AFZ05510 |
| o | *Oscillatoria* sp. PCC 6506 | 96.1 | 77.4 | OSCI_940017 | CBN54532 |
| | *Dactylococcopsis salina* PCC 8305 | 96.1 | 77.0 | Dacsa_2178 | AFZ50804 |
| | *Chamaesiphon minutus* PCC 6605 | 93.9 | 76.6 | Cha6605_4153 | AFY95099 |
| | *Leptolyngbya* sp. O-77 | 94.8 | 76.1 | O77CONTIG1_03123 | BAU43295 |
| | *Trichodesmium erythraeum* IMS101 | 96.1 | 75.8 | Tery_2280 | ABG51506 |
| | *Pseudanabaena* sp. PCC 7367 | 93.5 | 75.3 | Pse7367_3626 | AFY71859 |
| o | *Planktothrix agardhii* NIV-CYA | 94.3 | 75.2 | A19Y_4321 | KEI68998 |
| | *Leptolyngbya boryana* IAM M-101 | 96.5 | 74.8 | LBWT_14420 | LBWT_14420(KEGG)* |
| | *Leptolyngbya* sp. NIES-3755 | 96.5 | 74.8 | LEP3755_23570 | BAU11854 |
| | *Halothece* sp. PCC 7418 | 95.6 | 74.4 | PCC7418_0961 | AFZ43170 |
| | *Acaryochloris marina* MBIC11017 | 92.6 | 74.4 | AM1_4041 | ABW29023 |
| | *Microcystis panniformis* FACHB-1757 | 93.5 | 74.4 | VL20_1523 | AKV66681 |
| | *Synechocystis* sp. PCC 6714 | 95.6 | 73.5 | D082_05310 | AIE73060 |
| | *Candidatus Atelocyanobacterium thalassa* | 93.9 | 73.5 | ucyna2_01151 | KFF41020 |
| | *Synechocystis* sp. PCC 6803 PCC-P | 95.6 | 73.2 | Sll0208 | SYNPCCP_2250 (KEGG)* |
| | *Synechocystis* sp. PCC 6803 PCC-N | 95.6 | 73.1 | Sll0208 | SYNPCCN_2250 (KEGG)* |

TABLE 2-continued

| Alkane-synthesizing capacity | Organism | Similarity (%) | Identity (%) | Gene | GenBank accession No. |
|---|---|---|---|---|---|
| | Synechocystis sp. PCC 6803 GT-I | 95.6 | 73.1 | Sll0208 | SYNGTI_2251 (KEGG)* |
| | Microcystis aeruginosa NIES-843 | 93 | 73.1 | MAE_53090 | BAG05131 |
| ○ | Synechocystis sp. PCC 6803 | 95.6 | 73.1 | Sll0208 | BAA10217 |
| | Thermosynechococcus sp. NK55 | 93.9 | 72.7 | NK55_03185 | AHB87984 |
| | Synechococcus sp. UTEX 2973 | 93 | 72.7 | M744_09020 | M744_09020(KEGG)* |
| | Synechococcus elongatus PCC6301 | 93 | 72.7 | syc0050_d | BAD78240 |
| ○ | Synechococcus elongatus PCC7942 | 93 | 72.7 | Synpcc7942_1593 | ABB57623 |
| ○ | Thermosynechococcus elongatus BP-1 | 94.3 | 72.7 | tll1313 | BAC08865 |
| | Synechococcus sp. PCC 7502 | 95.2 | 72.4 | Syn7502_03278 | AFY75144 |
| | Synechococcus sp. PCC 6312 | 96 | 71.7 | Syn6312_2280 | AYF64395 |
| | Geminocystis sp. NIES-3708 | 93.4 | 71.7 | GM3708_2118 | BAQ61712 |
| | Cyanobacterium aponinum PCC 10605 | 93.4 | 70.8 | Cyan10605_1692 | AFZ53795 |
| ○ | Cyanothece sp. PCC 7425 | 96.1 | 70.5 | Cyan7425_0398 | ACL42790 |
| ○ | Anabaena variabilis ATCC 29413 | 96.1 | 70.5 | Ava_2533 | ABA22148 |
| | Cyanobacterium endosymbiont of Epithemia turgida | 93.5 | 70.1 | ETSB_0877 | BAP17683 |
| | Synechococcus sp. JA-2-3B'a(2-13) | 92.6 | 66.3 | CYB_2442 | ABD03376 |
| ○ | Synechococcus sp. JA-3-3Ab | 91.8 | 65.0 | CYA_0415 | ABC98634 |
| ○ | Synechocystis sp. RS9917 | 90 | 63.6 | RS9917_09941 | EAQ69748 |
| | Gloeobacter kilaueensis JS1 | 90.5 | 62.9 | GKIL_0725 | AGY56971 |
| | Synechococcus sp. WH7803 | 86.5 | 62.7 | SynWH7803_0654 | CAK23080 |
| | Cyanobium gracile PCC 6307 | 89.1 | 61.9 | Cyagr_0039 | AFY27259 |
| | Synechococcus sp. KORDI-52 | 88.7 | 61.9 | KR52_13300 | AII50102 |
| | Synechococcus sp. WH 8109 | 88.7 | 61.4 | Syncc8109_1976 | AHF64320 |
| | Synechococcus sp. CC9605 | 88.7 | 61.4 | Syncc9605_0728 | ABB34500 |
| | Synechococcus sp. KORDI-49 | 88.3 | 61.0 | KR49_12745 | AII47259 |
| | Synechococcus sp. CC9902 | 88.3 | 61.0 | Syncc9902_1635 | ABB26593 |
| | Synechococcus sp. KORDI-100 | 89.6 | 60.6 | KR100_05365 | AII42794 |
| | Synechococcus sp. WH8102 | 88.3 | 60.1 | SYNW1738 | CAE08253 |
| | Synechococcus sp. RCC307 | 88.3 | 59.7 | SynRCC307_1586 | CAK28489 |
| | Prochlorococcus marinus MIT 9303 | 90 | 59.3 | P9303_07791 | ABM77530 |
| | Synechococcus sp. CC9311 | 88.3 | 59.3 | sync_1990 | ABI47589 |
| ○ | Prochlorococcus marinus MIT 9313 | 89.6 | 58.8 | PMT_1231 | CAE21406 |
| | Cyanothece sp. PCC 7425 | 90.4 | 57.5 | Cyan7425_2986 | ACL45322 |
| | Prochlorococcus marinus MED4 | 88.2 | 56.5 | PMM0532 | CAE18991 |
| | Prochlorococcus marinus MIT 9515 | 87.8 | 55.6 | P9515_05961 | ABM71805 |
| | Prochlorococcus marinus MIT 9301 | 86.9 | 55.2 | P9301_05581 | ABO1718 |
| | Prochlorococcus marinus AS9601 | 87.3 | 55.2 | A9601_05881 | ABM69874 |
| | Prochlorococcus marinus MIT 9215 | 87.3 | 55.2 | P9215_06131 | ABV50228 |
| | Prochlorococcus marinus MIT 9312 | 87.3 | 54.7 | PMT9312_0532 | ABB49593 |
| | Prochlorococcus p. MIT 0604 | 87.3 | 54.3 | EW14_0578 | AIQ94601 |
| | Prochlorococcus marinus MIT 9211 | 88.6 | 53.9 | P9211_05351 | ABX08466 |
| | Prochlorococcus marinus NATL 1A | 87.8 | 53.4 | NATL1_05881 | ABM75150 |
| ○ | Prochlorococcus marinus NATL2A | 87.8 | 53.4 | PMN2A_1863 | AAZ59351 |
| | Prochlorococcus sp. MIT 0801 | 88.2 | 53.0 | EW15_0629 | AIQ96721 |
| | Prochlorococcus marinus SS120 | 87.8 | 51.3 | Pro_0532 | AAP99577 |

(KEGG)*KEGG entry number

In Table 2, microorganisms indicated with the symbol "○" in the "alkane-synthesizing capacity" column were found to have the alkane-synthesizing capacity in a reference. The nucleotide sequences of the coding regions of the decarbonylase genes of the microorganisms shown in Table 2 and the amino acid sequences encoded thereby can be obtained from the GenBank database or other databases on the basis of the names and the GenBank accession numbers shown in Table 2.

Concerning the decarbonylases derived from the microorganisms shown in Table 2, the amino acid sequences obtained from the databases and the amino acid sequence as shown in SEQ ID NO: 2 are subjected to pairwise alignment analysis. Thus, the amino acid residues to be substituted can be identified. Among the amino acid residues to be substituted, for example, glycine 90 in the amino acid sequence as shown in SEQ ID NO: 2 may not be in the position 90 in an amino acid sequence of the decarbonylases derived from the microorganisms shown in Table 2. In addition, an amino acid residue in the corresponding position may be an amino acid other than glycine. In the amino acid sequence of the decarbonylases derived from the microorganisms shown in Table 2, in such a case, an amino acid residue at a position corresponding to glycine 90 in the amino acid sequence as shown in SEQ ID NO: 2 is to be substituted. When an expression such as "an amino acid corresponding to glycine 90" is used herein, such expression encompasses both glycine 90 in the amino acid sequence as shown in SEQ ID NO: 2 and an amino acid located at a position corresponding to glycine 90 in an amino acid sequence different from the amino acid sequence as shown in SEQ ID NO: 2.

As described above, amino acids to be substituted in the amino acid sequence as shown in SEQ ID NO: 2 are glycine 90, cysteine 107, serine 163, and asparagine 171. In the amino acid sequences of the decarbonylases derived from the microorganisms shown in Table 2, accordingly, amino acids to be substituted are an amino acid residue corresponding to glycine 90 in the amino acid sequence as shown in SEQ ID NO: 2, an amino acid residue corresponding to cysteine 107 in the amino acid sequence as shown in SEQ ID NO: 2, an amino acid residue corresponding to serine 163 in the amino acid sequence as shown in SEQ ID NO: 2, and an amino acid residue corresponding to asparagine 171 in the amino acid sequence as shown in SEQ ID NO: 2.

In the decarbonylases derived from the microorganisms shown in Table 2, the amino acid residues after substitution can be selected from among amino acids exhibiting a higher degree of hydrophobicity than the amino acid residues before substitution as with the case of the decarbonylase comprising the amino acid sequence as shown in SEQ ID NO: 2. In some embodiments, the amino acid residue after the mutation may be selected from the group consisting of phenylalanine (F), leucine (L), valine (V), and isoleucine (I).

Concerning the mutant decarbonylase gene, at least one amino acid residue selected from among an amino acid residue corresponding to glycine 90 in the amino acid sequence as shown in SEQ ID NO: 2, an amino acid residue corresponding to cysteine 107 in the amino acid sequence as shown in SEQ ID NO: 2, an amino acid residue corresponding to serine 163 in the amino acid sequence as shown in SEQ ID NO: 2, and an amino acid residue corresponding to asparagine 171 in the amino acid sequence as shown in SEQ ID NO: 2 may be substituted. Specifically, the mutant decarbonylase gene may involve substitution of arbitrary 2, 3, or 4 amino acid residues selected from among the target amino acid residues mentioned above.

There are four other examples of decarbonylase genes encoding a decarbonylase: (1) decarbonylases typified by Npun_R1711 of *Nostoc punctiforme* (Science mentioned above); (2) a decarbonylase related to an aldehyde dehydrogenase (JP Patent No. 5,867,586); (3) long-chain alkane synthases typified by the Cer1 gene of *Arabidopsis thaliana* (Plant Cell, 24, 3106-3118, 2012); and (4) P450 alkane synthases typified by the CYP4G1 gene of *Drosophila melanogaster* (PNAS, 109, 37, 14858-14863, 2012).

More specific examples of (1) include Npun_R0380 of *Nostoc punctiforme* (a paralog of Npun_R1711), Nos7524_4304 of *Nostoc* sp., Anacy_3389 of *Anabaena cylindrica*, Aazo_3371 of *Anabaena azollae*, Cylst_0697 of *Cylindrospermum stagnale*, Glo7428_0150 of *Gloeocapsa* sp., Cal7507_5586 of *Calothrix* sp., FIS3754_06310 of *Fischerella* sp., Mic7113_4535 of *Microcoleus* sp., Chro_1554 of *Chroococcidiopsis thermalis*, GEI7407_1564 of *Geitlerinema* sp., and Cyan8802_0468 of *Cyanothece* sp.

Specific examples of (2) include: BAE77705, BAA35791, BAA14869, BAA14992, BAA15032, BAA16524, BAE77705, BAA15538, and BAA15073 derived from *Escherichia coli* K-12 W3110; YP_001268218, YP_001265586, YP_001267408, YP_001267629, YP_001266090, YP_001270490, YP_001268439, YP_001267367, YP_001267724, YP_001269548, YP_001268395, YP_001265936, YP_001270470, YP_001266779, and YP_001270298 derived from *Pseudomonas putida*_F1; NP_388129, NP_389813, NP_390984, NP_388203, NP_388616, NP_391658, NP_391762, NP_391865, and NP_391675 derived from *Bacillus subtilis* 168; NP_599351, NP_599725, NP_601988, NP_599302, NP_601867, and NP_601908 derived from *Corynebacterium glutamicum* ATCC13032; YP_001270647 derived from *Lactobacillus reuteri* DSM20016; NP_010996, NP_011904, NP_015264, NP_013828, NP_009560, NP_015019, NP_013893, NP_013892, and NP_011902 derived from *Saccharomyces cerevisiae*; XP_002548035, XP_002545751, XP_002547036, XP_002547030, XP_002550712, XP_002547024, XP_002550173, XP_002546610, and XP_002550289 derived from *Candida tropicalis* MYA-3404; XP_460395, XP_457244, XP_457404, XP_457750, XP_461954, XP_462433, XP_461708, and XP_462528 derived from *Debaryomyces hansenii* CBS767; XP_002489360, XP_002493450, XP_002491418, XP_002493229, XP_002490175, XP_002491360, and XP_002491779 derived from *Pichia pastoris* GS115; NP_593172, NP_593499, and NP_594582 derived from *Schizosaccharomyces pombe*; XP_001822148, XP_001821214, XP_001826612, XP_001817160, XP_001817372, XP_001727192, XP_001826641, XP_001827501, XP_001825957, XP_001822309, XP_001727308, XP_001818713, XP_001819060, XP_001823047, XP_001817717, and XP_001821011 derived from *Aspergillus oryzae* RIB40; NP_001150417, NP_001105047, NP_001147173, NP_001169123, NP_001105781, NP_001157807, NP_001157804, NP_001105891, NP_001105046, NP_001105576, NP_001105589, NP_001168661, NP_001149126, and NP_001148092 derived from *Zea mays*; NP_564204, NP_001185399, NP_178062, NP_001189589, NP_566749, NP_190383, NP_187321, NP_190400, NP_001077676, and NP_175812 derived from *Arabidopsis thaliana*; NP_733183, NP_609285, NP_001014665, NP_649099, NP_001189159, NP_610285, and NP_610107 derived from *Drosophila melanogaster*; NP_001006999, XP_001067816, XP_001068348, XP_001068253, NP_113919, XP_001062926, NP_071609, NP_071852, NP_058968, NP_001011975, NP_115792, NP_001178017, NP_001178707, NP_446348, NP_071992, XP_001059375, XP_001061872, and NP_001128170 derived from *Rattus norvegicus*; NP_036322, NP_001193826, NP_001029345, NP_000684, NP_000680, NP_000683, NP_000681, NP_001071, NP_000687, NP_001180409, NP_001173, NP_000682, NP_000373, NP_001154976, NP_000685, and NP_000686 derived from *Homo sapiens*; and KPN_02991, KPN_1455, and KPN_4772 derived from *Klebsiella* sp. NBRC100048.

Specific examples of (3) include: AT1G02190 and AT1G02205 (CER1) of *Arabidopsis thaliana;* 4330012 of *Oryza sativa;* 101252060 of *Solanum lycopersicum*; CARUB_v10008547 mg of *Capsella rubella;* 106437024 of *Brassica napus;* 103843834 of *Brassica rapa;* EUT-SA_v10009534 mg of *Eutrema salsugineum;* 104810724 of *Tarenaya hassleriana;* 105773703 of *Gossypium raimondii;* TCM_042351 of *Theobroma cacao;* 100243849 of *Vitis vinifera;* 105167221 of *Sesamum indicum;* 104442848 of *Eucalyptus grandis;* 103929751 of *Pyrus bretschneideri;* 107618742 of *Arachis ipaensis;* and 103428452 of *Malus domestica.*

Specific examples of (4) include CYP4G1 of *Drosophila melanogaster,* 101887882 of *Musca domestica,* AaeL_AAEL006824 of *Aedes aegypti*, and AgaP_AGAP000877 of *Anopheles gambiae.*

The various types of decarbonylase genes described above can be mutant decarbonylase genes each encoding a decarbonylase mutant comprising an amino acid sequence derived from the amino acid sequence as shown in SEQ ID NO: 2 by the substitution mutation defined above. Also, the mutant decarbonylase genes derived from the various types of decarbonylase genes described above each encode a decarbonylase mutant with enhanced decarbonylase activity.

As described above, the mutant decarbonylase gene according to the present disclosure is introduced into a host microorganism together with an acyl-ACP reductase gene that catalyzes conversion of acyl-ACP into fatty aldehyde or it is introduced into a host microorganism comprising the acyl-ACP reductase gene. Thus, a recombinant microorganism having the alkane-producing capacity can be prepared.

The acyl-ACP reductase gene is not particularly limited, and a gene encoding the acyl-ACP reductase registered as EC 1.2.1.80 can be used. Examples of acyl-ACP reductase genes include Synpcc7942_1594 of *Synechococcus elongatus*, M744_09025 of *Synechococcus* sp., LEP3755_23580 of *Leptolyngbya* sp., Glo7428_0151 of *Gloeocapsa* sp., Nos7107_1027 of *Nostoc* sp., Ava_2534 of *Anabaena variabilis*, IJ00_07395 of *Calothrix* sp., Cri9333_4415 of *Crinalium epipsammum*, and FIS3754_06320 of *Fischerella* sp.

For example, the acyl-ACP reductase gene derived from *Synechococcus elongatus* PCC 7942 encodes a protein comprising the amino acid sequence as shown in SEQ ID NO: 4. The acyl-ACP reductase gene may comprise an amino acid sequence exhibiting 60%, 70%, 80%, 90%, 95%, or 98% or higher identity to the amino acid sequence as shown in SEQ ID NO: 4 and encode a protein having acyl-ACP reductase activity.

The degree of sequence identity can be determined using the BLASTN or BLASTX Program equipped with the BLAST algorithm (at default settings). The degree of sequence identity is determined by subjecting a pair of amino acid sequences to pairwise alignment analysis, identifying completely identical amino acid residues, and calculating the percentage of all the amino acid residues subjected to comparison accounted for by such amino acid residues.

The acyl-ACP reductase gene is not limited to a gene encoding the amino acid sequence as shown in SEQ ID NO: 4. It may be a gene comprising an amino acid sequence derived from the amino acid sequence as shown in SEQ ID NO: 4 by deletion, substitution, addition, or insertion of 1 to 50, 1 to 40, 1 to 30, or 1 to 20 amino acids and encoding a protein functioning as an acyl-ACP reductase.

Furthermore, the acyl-ACP reductase gene is not limited to a gene comprising the nucleotide sequence as shown in SEQ ID NO: 3. For example, it may be a gene hybridizing under stringent conditions to the full-length sequence or a partial sequence of a complementary strand of DNA comprising the nucleotide sequence as shown in SEQ ID NO: 3 and encoding a protein functioning as an acyl-ACP reductase. Under "stringent conditions," so-called specific hybrids are formed, but non-specific hybrids are not formed. For example, such conditions can be adequately determined with reference to Molecular Cloning: A Laboratory Manual (Third Edition). Specifically, the degree of stringency can be determined in accordance with the temperature and the salt concentration of a solution used for Southern hybridization and the temperature and the salt concentration of a solution used for the step of washing in Southern hybridization.

A method for preparing DNA comprising a nucleotide sequence encoding an amino acid sequence derived from the amino acid sequence as shown in SEQ ID NO: 4 by deletion, substitution, addition, or insertion of given amino acids or DNA comprising a nucleotide sequence different from the nucleotide sequence as shown in SEQ ID NO: 3 is not particularly limited, and a known method can be adequately adopted. For example, given nucleotides can be substituted by a site-directed mutagenesis technique. Examples of site-directed mutagenesis techniques include a method of site-directed mutagenesis (i.e., the Kunkel method, T. Kunkel, T. A., Proc. Nati. Acad. Sci., U.S.A., 82, 488-492, 1985) and the Gapped duplex method. Alternatively, a mutation can be introduced with the use of, for example, a mutagenesis kit that adopts a site-directed mutagenesis technique (e.g., Mutan-K and Mutan-G, manufactured by TAKARA SHUZO CO., LTD.) or an LA PCR in vitro Mutagenesis series kit manufactured by TAKARA SHUZO CO., LTD.

In place of the acyl-ACP reductase gene, a gene encoding an enzyme that synthesizes aldehyde serving as a substrate for the decarbonylase mutant can be used.

For example, a gene encoding a long chain fatty acyl-CoA reductase (EC. 1.2.1.50), such as plu2079 (luxC) of *Photorhabdus luminescens*, PAU_02514 (luxC) of *Photorhabdus asymbiotica*, VF_A0923 (luxC) of *Aliivibrio fischeri*, VIBHAR_06244 of *Vibrio campbellii*, or Swoo_3633 of *Shewanella woodyi*, can be used. Also, genes encoding acyl-CoA reductases described in JP 2015-226477 A, such as 100776505 and 100801815 of *Glycine max*, can be used. In addition, any gene encoding an enzyme that can synthesize an aldehyde can be used without particular limitation. For example, genes encoding enzymes, such as alcohol dehydrogenase (EC.1.1.1.1), alcohol oxidase (EC. 1.1.3.13), aldehyde dehydrogenase (EC. 1.2.1.3), and carboxylate reductase (EC. 1.2.99.6), can be used.

Microorganisms into which the mutant decarbonylase gene is to be introduced are not particularly limited, and examples include bacteria of the genera *Escherichia* and *Klebsiella*. As microorganisms into which the mutant decarbonylase gene is to be introduced, *Corynebacterium glutamicum* disclosed in Appl. Environ. Microbiol., 79 (21): 6776-6783, 2013 (November) can be used. This literature discloses a recombinant *Corynebacterium glutamicum* that has acquired the fatty acid-producing capacity. As microorganisms into which the mutant decarbonylase gene is to be introduced, in addition, *Mortierella alpina* disclosed in Food Bioprocess Technol., 2011, 4: 232-240 can be used. *Mortierella alpina* is used at the industrial level for arachidonic acid fermentation, and, in this literature, metabolic engineering is practiced with the use thereof. In addition, *Yarrowia lipolytica* disclosed in TRENDS IN BIOTECHNOLOGY, Vol. 34, No. 10, pp. 798-809 can be used as a microorganism into which the mutant decarbonylase gene is to be introduced.

As microorganisms into which the mutant decarbonylase gene is to be introduced, microorganisms belonging to the genera *Lipomyces, Pseudozyma, Rhodosporidium*, and *Rhodococcus* can be used. In order to introduce the alkane synthase gene into such microorganisms, a gene recombination technique involving the genome editing system, such as CRISPR/Cas or TALEN, can be adopted without particular limitation.

When yeast strains are used as microorganisms into which the mutant decarbonylase gene is to be introduced, examples of yeast strains that can be used include, but are not particularly limited to, a yeast strain that belongs to the genus *Pichia* such as *Pichia stipitis*, a yeast strain that belongs to the genus *Saccharomyces* such as *Saccharomyces cerevisiae*, and yeast strains that belong to the genus *Candida* such as *Candida tropicalis* and *Candida prapsilosis*.

When the mutant decarbonylase gene, the acyl-ACP reductase gene, and other genes are introduced into hosts, for example, a DNA fragment containing the mutant decarbonylase gene or the acyl-ACP reductase gene may be inserted into an expression vector that can function in a host microorganism (e.g., a multiple-copy vector) to prepare recombinant DNA, and the resulting recombinant DNA may then be introduced into a microorganism to transform the microorganism. Expression vectors that can be used are not particularly limited, and a plasmid vector or a chromosome transfer vector that can be incorporated into the genome of the host organism can be used. An expression vector is not particularly limited, and an available expression vector may be adequately selected in accordance with a host microorganism. Examples of expression vectors include plasmid DNA, bacteriophage DNA, retrotransposon DNA, and yeast artificial chromosome (YAC) DNA.

Examples of plasmid DNA include: YCp-type *E. coli*-yeast shuttle vectors, such as pRS413, pRS414, pRS415, pRS416, YCp50, pAUR112, and pAUR123; YEp-type *E. coli*-yeast shuttle vectors, such as pYES2 and YEp13; YIp-type *E. coli*-yeast shuttle vectors, such as pRS403, pRS404, pRS405, pRS406, pAUR101, and pAUR135; *E. coli*-derived plasmids (e.g., ColE plasmids, such as pBR322, pBR325, pUC18, pUC19, pUC118, pUC119, pTV118N, pTV119N, pBluescript, pHSG298, pHSG396, and pTrc99A, p15A plasmids, such as pACYC177 and pACYC184, and pSC101 plasmids, such as pMW118, pMW119, pMW218, and pMW219); *Agrobacterium*-derived plasmids (e.g., pBI101); and *Bacillus subtilis*-derived plasmids (e.g., pUB110 and pTP5). Examples of phage DNA include λ phage (e.g., Charon4A, Charon21A, EMBL3, EMBL4, λgt10, λgt11, and λZAP), φX174, M13mp18, and M13mp19. An example of retrotransposon is a Ty factor. An example of a YAC vector is pYACC2. In addition, animal virus vectors, such as retrovirus or vaccinia virus vectors, and insect virus vectors, such as baculovirus vectors, can be used.

It is necessary that the mutant decarbonylase gene be incorporated into an expression vector in an expressible state. In an expressible state, the mutant decarbonylase gene is bound to a promoter, and the resultant is incorporated into a vector in that state, so that the mutant decarbonylase gene is expressed under the control of a given promoter in a host organism. In addition to the mutant decarbonylase gene, a promoter, a terminator, a cis element such as an enhancer according to need, a splicing signal, a poly A addition signal, a selection marker, a ribosome binding sequence (SD sequence), and the like can be bound to the expression vector. Examples of selection markers include antibiotic resistant genes, such as ampicillin resistant gene, kanamycin resistant gene, and hygromycin resistant gene.

As a method of transformation involving the use of an expression vector, a conventional technique can be adequately employed. Examples of methods of transformation include the calcium chloride method, the competent cell method, the protoplast or spheroplast method, and the electropulse method.

Meanwhile, the mutant decarbonylase gene may be introduced to increase the number of copies thereof. Specifically, the mutant decarbonylase gene may be introduced in a manner such that multiple copies of the mutant decarbonylase genes would be present in chromosome DNA of the microorganism. Multiple copies of the mutant decarbonylase genes can be introduced into chromosome DNA of the microorganism via homologous recombination with the use of multiple copies of target sequences that are present in chromosome DNA.

The mutant decarbonylase gene expression level can be elevated by, for example, a method in which an expression regulatory sequence such as a promoter of the introduced mutant decarbonylase gene is substituted with a sequence that can express the gene of interest at a higher level or a method in which a regulator to elevate the expression level of a given gene is introduced. Examples of promoters that enable high level gene expression include, but are not particularly limited to, lac promoter, trp promoter, trc promoter, and pL promoter. Alternatively, a mutation may be introduced into an expression regulatory region of the endogenous or introduced ferredoxin gene or the ferredoxin reductase gene to modify the gene to be expressed at a higher level.

<Alkane Production>

As described above, alkane can be synthesized with excellent productivity with the use of a recombinant microorganism into which the mutant decarbonylase gene has been introduced.

In a system involving the use of recombinant microorganisms comprising the mutant decarbonylase gene introduced thereinto, culture can be conducted in a medium suitable for such microorganisms, and alkane can be produced in the medium. According to the present disclosure, more specifically, the alkane-synthesizing capacity with the aid of an alkane synthase can be improved, and alkane productivity can be improved as a consequence.

According to the present disclosure, alkane to be produced may have, for example, 9 to 20, 14 to 17, or 13 to 16 carbon atoms, although the number of carbon atoms is not limited thereto. Alkane is a solution with high viscosity, and it can be used for light oil (diesel oil) or aircraft fuel. Such alkane can be isolated from a reaction system in which the recombinant microorganisms were cultured in accordance with a conventional technique and then purified. By adopting the method described in Engineering in Life Sciences, vol. 16:1, pp. 53-59, "Biosynthesis of chain-specific alkanes by metabolic engineering in *Escherichia coli*," short-chain alkane can be synthesized.

EXAMPLES

Hereafter, the present disclosure is described in greater detail with reference to the examples, although the technical scope of the present disclosure is not limited to the following examples.

Example 1

[1. Objective]

A decarbonylase is a key enzyme used when producing alkane (hydrocarbon), which is a next-generation biodiesel fuel, via fermentation with the aid of microorganisms such as *Escherichia coli*. In order to develop a technique of enhancing enzyme activity of a decarbonylase, in this example, a substitution mutation of amino acids aimed at strengthening a hydrophobic bond between α helix structures was introduced into a decarbonylase to prepare a decarbonylase mutant, and the mutation of amino acids that would enhance decarbonylase activity was identified.

[2. Materials and Method]

2.1: Reagent

The plasmids used in the example: i.e., pRSF-Duet-1 and pCDF-Duet-1, were purchased from Novagen. In this example, reagents that are not specified by the manufacturers were purchased from Nacalai tesque.

2.2: Strains

In this example, *E. coli* BL-21 purchased from Takara Bio Inc. and *E. coli* JM109 purchased from Nippon Gene Co., Ltd. were used.

2.3: Preparation of Plasmids 2.3.1: Preparation of pRSF-NpAD-PA

At the outset, pRSF-NpAD-SeAR was prepared in the manner described below. Specifically, the acyl-ACP reductase gene derived from *Synechococcus elongatus* PCC 7942 (YP_400611) and the decarbonylase gene derived from *Nostoc punctiforme* PCC 73102 (YP_001865325) were chemically synthesized. These synthetic genes were inserted into the EcoRV site of pUC57 and designated as pUC57-SeAAR and pUC57-NpAD, respectively.

Subsequently, pUC57-NpAD and pUC57-SeAAR were used as templates to perform PCR with the use of Pfu Ultra II Fusion HS DNA Polymerase (STRATAGENE) in the manner described below, and the amplified fragments; i.e., NpADvo and SeAAvo, were obtained.

TABLE 3

| Reaction composition: | |
|---|---|
| pUC57-NpAD (30 ng/µl) | 1 µl |
| 10x Pfu Ultra II reaction buffer | 5 µl |
| dNTP mix (25 mM each) | 1 µl |
| Primer pRSF-NpAS-inf-F (10 µM) | 2 µl |
| Primer pRSF-NpAS-inf-R (10 µM) | 2 µl |
| Pfu Ultra II fusion HS DNA polymerase | 1 µl |
| Sterilized deionized water | 38 µl |
| Total | 50 µl |

TABLE 4

| Reaction composition: | |
|---|---|
| pUC57-SeAAR (1 ng/µl) | 1 µl |
| 10x Pfu Ultra II reaction buffer | 5 µl |
| dNTP mix (25 mM each) | 1 µl |
| Primer pRSF-SeAR-inf-F (10 µM) | 2 µl |
| Primer pRSF-SeAR-inf-R (10 µM) | 2 µl |
| Pfu Ultra II fusion HS DNA polymerase | 1 µl |
| Sterilized deionized water | 38 µl |
| Total | 50 µl |

PCR temperature conditions comprises: 92° C. for 2 minutes, a cycle of 92° C. for 10 seconds, 55° C. for 20 seconds, and 68° C. for 5 minutes repeated 25 times, 72° C. for 3 minutes, and 16° C. Primer sequences are as shown below.

```
Primer pRSF-NpAS-inf-F:
                                      (SEQ ID NO: 5)
5'-cgagctcggcgcgcctgcagATGCAGCAGCTTACAGACCA-3'

Primer pRSF-NpAS-inf-R:
                                      (SEQ ID NO: 6)
5'-gcaagcttgtcgacctgcagTTAAGCACCTATGAGTCCGT-3'

Primer pRSF-SeAR-inf-F:
                                      (SEQ ID NO: 7)
5'-aaggagatatacatatgATGTTCGGTCTTATCGGTCA-3'

Primer pRSF-SeAR-inf-R:
                                      (SEQ ID NO: 8)
5'-ttgagatctgccatatgTCAAATTGCCAATGCCAAGG-3'
```

Subsequently, PstI-treated pRSF-1b (Novagen) was ligated to the NpADvo fragment using the In-Fusion HD Cloning kit (Invitrogen), the resulting plasmid was further digested with NdeI, and the resultant was bound to the SeAAvo fragment using the aforementioned kit. The vector thus obtained was designated as pRSF-NpAD-SeAR.

PCR was then carried out under the conditions described below using the resulting pRSF-NpAD-SeAR as a template.

TABLE 5

| Reaction composition: | |
|---|---|
| pRSF-NpAD-SeAR (1 ng/µl) | 1 µl |
| 10x Pfu Ultra II reaction buffer | 5 µl |
| dNTP mix (25 mM each dNTP) | 0.5 µl |
| Primer Fw1 (10 µM) | 0.5 µl |
| Primer Rv1 (10 µM) | 0.5 µl |
| Pfu Ultra II fusion HS DNA polymerase | 1 µl |
| Sterilized water | 41.5 µl |
| Total | 50 µl |

PCR temperature conditions comprises: 95° C. for 2 minutes, a cycle of 95° C. for 20 seconds, 55° for 20 seconds, and 72° C. for 30 seconds repeated 25 times, and 72° C. for 3 minutes. Primer sequences are as shown below.

```
Primer FW1:
                                      (SEQ ID NO: 9)
AGGAGATATACCATGCAGCAGCTTACAGACC Primer Rv1:
                                      (SEQ ID NO: 10)
GCTCGAATTCGGATCTTACACCACATCATCTTCGGCACCTGGCATGG

CAACGCCAGCACCTATGAGTCCGTAGG
```

Subsequently, the PCR-amplified DNA fragment was inserted into a region between the NcoI site and the BamHI site of pRSF-Duet-1 using the In-Fusion HD Cloning kit (Clontech Laboratories, Inc.). The resulting plasmid was designated as pRSF-NpAD-PA.

2.3.2: Preparation of pCDF-SeAR

Also, PCR was carried out under the conditions described below using pRSF-NpAD-SeAR as a template.

TABLE 6

| Reaction composition: | |
|---|---|
| pRSF-NpAD-SeAR (1 ng/µl) | 1 µl |
| 10x Pfu Ultra II reaction buffer | 5 µl |
| dNTP mix (25 mM each dNTP) | 1 µl |
| Primer Fw2 (10 µM) | 2 µl |
| Primer Rv2 (10 µM) | 2 µl |
| Pfu Ultra II fusion HS DNA polymerase | 1 µl |
| Sterilized water | 38 µl |
| Total | 50 µl |

PCR temperature conditions comprises: 92° C. for 2 minutes, a cycle of 92° C. for 10 seconds, 55° for 20 seconds, and 68° C. for 5 minutes repeated 25 times, and 72° C. for 3 minutes. Primer sequences are as shown below.

```
Primer FW2:
                                      (SEQ ID NO: 11)
AAGGAGATATACATATGATGTTCGGTCTTATCGGTCA Primer Rv2:
                                      (SEQ ID NO: 12)
TTGAGATCTGCCATATGTCAAATTGCCAATGCCAAGG
```

Subsequently, the PCR-amplified DNA fragment was inserted into the NdeI site of pCDD-Duet-1 using the In-Fusion HD Cloning kit (Clontech Laboratories, Inc.). The resulting plasmid was designated as pCDF-SeAR.

2.3.3: Preparation of Plasmid for NpAD Mutant Gene Expression

Subsequently, PCR was carried out under the conditions described below with the use of the pRSF-NpAD-PA obtained above as a template and a set of primers capable of introducing a substitution mutation into a given site. The sets of primers used in this example are summarized in Table 8.

TABLE 7

| Reaction composition: | |
|---|---|
| pRSF-NpAD-PA (10 ng/µl) | 0.5 µl |
| 2x PrimeStar Max Premix | 12.5 µl |
| Fw shown in Tables 6 to 8 (10 µM) | 0.5 µl |
| Rv shown in Tables 6 to 8 (10 µM) | 0.5 µl |
| PrimeStar DNA polymerase | 1 µl |
| Sterilized water | 10 µl |
| Total | 25 µl |

PCR temperature conditions comprises: a cycle of 98° C. for 10 seconds, 58° for 15 seconds, and 72° C. for 30 seconds repeated 30 times.

TABLE 8

| Plasmid | Site of mutation | Primer | Primer sequence | SEQ ID NO: |
|---|---|---|---|---|
| No. 201 | Y40F | Fw | NpAD_Y40F-F GAAAATTTTATCACAC TAGCCCAACTGCTGCC | SEQ ID NO: 13 |
| | | Rv | NpAD_Y40F-R TGTGATAAAATTTTCATG GGCTTCTTGTTCCCCTTC | SEQ ID NO: 14 |
| No. 202 | T42F | Fw | NpAD_T42F-F TACATCTTTCTAGCCCAA CTGCTGCCAGAATC | SEQ ID NO: 15 |
| | | Rv | NpAD_T42F-R GGCTAGAAAGATGTAATTTT CATGGGCTTCTTGTTCCC | SEQ ID NO: 16 |
| No. 203 | A44V | Fw | NpAD_A44V-F ACACTAGTGCAACTGC TGCCAGAATCTCATG | SEQ ID NO: 17 |
| | | Rv | NpAD_A44V-R CAGTTGCACTAGTGTGAT GTAATTTTCATGGGCTTC | SEQ ID NO: 18 |
| No. 204 | G90V | Fw | NpAD_G90V-F TTCTCCGTGCTACACCA AAATTTTCAAACAGCT | SEQ ID NO: 19 |
| | | Rv | NpAD_G90V-R GTGTAGCACGGAGAAA ACTCTTTGGCAAATTG | SEQ ID NO: 20 |
| No. 205 | C107V | Fw | NpAD_C107V-F GGTTACTGTGCTGTTGATTC AGTCTTTAATTATTGAATGT | SEQ ID NO: 21 |
| | | Rv | NpAD_C107V-R CAACAGCACAGTAA CCACTTTCCCTTCT | SEQ ID NO: 22 |
| No. 206 | S163V | Fw | NpAD_S163V-F GCAGAAGTGAAAGCT GAACTTGAACTTGC | SEQ ID NO: 23 |
| | | Rv | NpAD_S163V-R AGCTTTCACTTCTGCA AAGTGTTCTTTCAACC | SEQ ID NO: 24 |
| No. 207 | N171V | Fw | NpAD_N171V-F ACTTGCACTGCGCC AGAACCTACCCATC | SEQ ID NO: 25 |
| | | Rv | NpAD_N171V-R CTGGCGCAGTGCAA GTTCAAGTTCAGCT | SEQ ID NO: 26 |
| No. 208 | N174V | Fw | NpAD_N174V-F CAGAACGAACCCATCGT CTGGAAAATGCTCAAC | SEQ ID NO: 27 |
| | | Rv | NpAD_N174V-R GATGGGTTCGTTCTGGC GATTTGCAAGTTCAAG | SEQ ID NO: 28 |
| No. 209 | W179V | Fw | NpAD_W179V-F ATCGTCGTGAAAATGCTCA ACCAAGTAGAAGGTGATG | SEQ ID NO: 29 |
| | | Rv | NpAD_W179V-R CATTTTCACGACGATG GGTAGGTTCTGGCGA | SEQ ID NO: 30 |
| No. 210 | Q181V | Fw | NpAD_Q181V-F TGGAAAGTGCTCAAC CAAGTAGAAGGTGAT | SEQ ID NO: 31 |
| | | Rv | NpAD_Q181V-R GTTGAGCACTTTCC AGACGATGGGTAG | SEQ ID NO: 32 |
| No. 211 | Q184F | Fw | NpAD_Q184F-F CTCAACTTTGTAGAAGG TGATGCCCACACAATG | SEQ ID NO: 33 |
| | | Rv | NpAD_Q184F-R TTCTACAAAGTTGAGCAT TTTCCAGACGATGGGTAG | SEQ ID NO: 34 |
| No. 212 | A189V | Fw | NpAD_A189V-F GGTGATGTGCACAC AATGGCAATGGAA | SEQ ID NO: 35 |
| | | Rv | NpAD_A189V-R TGTGTGCACATCACC TTCTACTTGGTTGAG | SEQ ID NO: 36 |
| No. 213 | Y207F | Fw | NpAD_Y207F-F ATTCAGTTTGGTGAAG CATTGAGTAACATTG | SEQ ID NO: 37 |
| | | Rv | NpAD_Y207F-R CTTCACCAAACTGAATCA TGAAGTCTTCTACCAAA | SEQ ID NO: 38 |
| No. 214 | G208I | Fw | NpAD_G208I-F CAGTATATTGAAGCATTGAG TAACATTGGTTTTTCGACT | SEQ ID NO: 39 |
| | | Rv | NpAD_G208I-R CAATGCTTCAATATACTGAAT CATGAAGTCTTCTACCAAAG | SEQ ID NO: 40 |
| No. 215 | S212L | Fw | NpAD_S212L-F GCATTGCTGAACATT GGTTTTTCGACTCG | SEQ ID NO: 41 |
| | | Rv | NpAD_S212L-R CAATGTTCAGCAATGCT TCACCATACTGAATCAT | SEQ ID NO: 42 |

The 4.5-kb DNA fragment amplified via PCR was purified. With the use of the purified DNA fragment, the E. coli JM109 strain was transformed. The nucleotide sequences of the mutant decarbonylase genes included in the plasmids (No. 201 to No. 215) obtained from the transformant were determined to confirm the introduction of the mutation of interest and the absence of mutations in other regions.

2.4: Evaluation of Mutant Decarbonylase Gene

The E. coli BL-21 strain was transformed with the use of the plasmids Nos. 201 to 215 and pCDF-SeAR obtained above to prepare mutants. pRSF-NpAD-PA was used instead of the plasmids Nos. 201 to 215, and the transformants prepared with the use of pRSF-NpAD-PA and pCDF-SeAR were designated as wild-type strains. The wild-type strains and the transformants were cultured and the amounts of hydrocarbon production were quantitatively compared via MG/CMS.

In this example, the amount of hydrocarbon produced by the wild-type strain at O.D. 600 nm was designated to be 1, and the hydrocarbon-producing capacity of a transformant in which the mutant decarbonylase gene had been expressed was evaluated relative thereto.

Culture was conducted by first inoculating transformants into a 14-ml round tube (BD Falcon) containing 3 ml of the LB Broth Miller medium (Luria-Bertani, Difco) containing necessary antibiotics and performing agitation culture at 100 strokes/min for 18 hours at 37° C. using a three-tier culture vessel (MW-312, ABLE). The resulting preculture solution was inoculated at a concentration of 1% in 3 ml of an M9YE medium containing antibiotics, and culture was conducted with the use of a disposable glass test tube (φ16 mm×150 mm, manufactured by IWAKI) and the same culture vessel at 30° C. and 90 strokes/min for 2 or 3 days. In this culture, IPTG was added to a final concentration of 1 mM 4 hours after the transformants were inoculated.

Ethyl acetate (3 ml) was added to the equivalent amount of the culture solution 2 or 3 days after the initiation of culture and the resultant was blended using a vortex mixer for 10 seconds. After the mixture was centrifuged using a centrifuge (LC-230, TOMY) at room temperature and 2,000 rpm for 10 minutes, 1 ml of the ethyl acetate layer was transferred to a GC/MS vial, 10 ml of the internal standard solution (1 l/ml R-(−)-2-octanol/ethanol) was added thereto, and the vial was fastened.

A method of quantification via GC/MS is as described below. At the outset, recombinants grown on the agarose plate were inoculated into the 14-ml round tube (BD Falcon) containing 3 ml of the aforementioned medium, and culture was then conducted using a three-tier culture vessel (MW-312, ABLE) at 130 strokes/min for 18 hours at a given temperature. The resulting preculture solution was inoculated at a concentration of 1% in 3 ml of an M9YE medium containing antibiotics in a disposable glass test tube (φ16× 150 mm, IWAKI), culture was conducted in the same manner at 90 strokes/min for 4 hours, IPTG (final concentration: 1 mM) was added thereto, and culture was then conducted for an additional 3 days.

After the culture, 1.5 ml of the culture solution was fractionated in an Eppendorf tube and centrifuged using a small centrifuge (MX-301, TOMY) at 24° C. and 5800 g for 1 minute. The culture solution was removed while retaining 50 µl of the supernatant, and strains were suspended. Subsequently, 150 µl of ethyl acetate was added, the resultant was vigorously blended using a vortex mixer for multiple samples (Mixer 5432, Eppendorf) for 5 minutes, the resultant was centrifuged in the same manner at 24° C. and 13000 g for 1 minute, and 100 µl of the ethyl acetate layer was transferred to the GC/MS vial. Thereafter, 50 µl of the internal standard solution (0.4% (v/v) 2-octanol dissolved in 2-propanol) was added and the resultant was subjected to GC/MS (7890GC/5975MSD, Agilent). Analytical conditions are described below.

[Table 9]
<GC/MS Analysis Conditions>
Detector: MS
MS zone temperature
MS Quad: 150° C.
MS Source: 230° C.
Interface temperature: 260° C.
Column: Agilent HP-5MS (0.25 mm ϕ×30 m; film thickness: 0.25 µm)
Column temperature: retention at 60° C. for 1 min; temperature increase at 50° C./min; and
retention at 300° C. for 1 min
Inlet temperature: 250° C.
Amount of injection: 1 µl
Split ratio: 20:1
Carrier gas: He
Carrier gas flow rate: 1 ml/min
MS scan parameters
Low mass: 45
High mass: 350
Threshold: 30

[3. Results]

While a detailed description is omitted, the decarbonylase derived from the *Nostoc punctiforme* PCC73102 strain used in this example was subjected to homology modeling using SWISS-MODEL on the basis of the conformation data of the aldehyde deformylating oxigenase (KNUA011, 1.80 A) derived from *Oscillatoria* sp. The conformation of the obtained model was demonstrated using Mol Feet 5.0 (Fiat-Lux) to analyze the positional relationship among amino acid residues.

The results of modeling analysis were used to select candidate sites for a substitution mutation aimed at strengthening of a hydrophobic bond between the α helix structures constituting the decarbonylase and decarbonylase stabilization. Specifically, pairs of amino acid residues positioned to interact with each other (the distance between the residues: within 5 Å) were first selected on the basis of the results of modeling analysis. Among the selected pairs of amino acid residues, subsequently, the pairs positioned in the same α helix structure were excluded, and the pairs positioned outside the α helix structures were excluded. Also, amino acid residues binding to the aldehyde compound serving as a substrate and iron-binding amino acid residues (i.e., amino acid residues that may be associated with activity) were identified. From among the selected pairs of amino acid residues, those including amino acids positioned within 3 residues from the identified amino acid residues were excluded. From among the selected pairs of amino acid residues, in addition, those including amino acids positioned within 2 residues from the α helix terminus were excluded.

As described above, the pairs of amino acid residues positioned to interact with each other were identified, and pairs each comprising at least one hydrophilic amino acid were selected from among the amino acid residues determined above. The hydrophilic amino acid residues included in the selected pairs were designated as candidate amino acids to be substituted. Specifically, hydrophilic amino acid residues were amino acids other than phenylalanine (F), leucine (L), valine (V), and isoleucine (I) (see Table 1).

Amino acids after substitution were selected from among phenylalanine (F), leucine (L), valine (V), and isoleucine (I) as amino acids with high a high degree of hydrophobicity. In this example, in particular, conformational damage imposed on the amino acid after substitution was taken into consideration. When an amino acid residue to be substituted was tryptophan or tyrosine, in addition, phenylalanine was selected as the amino acid after substitution by further taking aromatic properties into consideration.

Thus, amino acid residues to be substituted and amino acids after substitution were selected, 15 types of mutant decarbonylase genes were prepared (Table 7), and the resultants were inserted into pRSF-Duet-1. The *E. coli* BL-21 strain was transformed with the use thereof and the pCDF-SeAR plasmid, and the amount of hydrocarbons (i.e., pentadecane and heptadecane) generated during culture was compared with that of the wild-type strain. The results are shown in FIG. 2.

As is apparent from FIG. 2, when 4 types of mutants; i.e., the mutant decarbonylase resulting from substitution of glycine 90 in the amino acid sequence as shown in SEQ ID NO: 2 with valine (hereafter referred to as the G90V mutant decarbonylase, the same applies to other substitutions), the C107V mutant decarbonylase, the S163V mutant decarbonylase, and the N171L mutant decarbonylase, were expressed in *E. coli*, the amount of hydrocarbons (i.e., pentadecane and heptadecane) generated was increased by at least 1.5 times.

When the G90V mutant decarbonylase was expressed in *E. coli*, in particular, it was found that the amount of hydrocarbons (i.e., pentadecane and heptadecane) generated was increased by 2.1 times. Glycine 90 as the amino acid to be substituted is positioned in a curved region of the α helix 3, and it is positioned to form a hydrophobic bond with isoleucine 177 of the α helix 7. The α helix 3 is positioned at the back of the active site formed of the α helices 1, 2, 5, and 4, and the α helix 7 is in a position associated with structural frame formation apart from the active site. Accordingly, the G90V mutation that had caused a hydrophobic bond formed between valine and isoleucine and improved stability of the structure composed of the α helix 3 and the α helix 7 is considered to impose insignificant influence on the structural change of the active site.

What is claimed is:

1. A mutant decarbonylase gene encoding a decarbonylase having at least one substitution mutation in the amino acid sequence as shown in SEQ ID NO: 2, wherein the mutation is selected from the group consisting of:
   a substitution mutation of an amino acid corresponding to glycine 90 with an amino acid exhibiting a higher degree of hydrophobicity than that of the amino acid to be substituted;
   a substitution mutation of an amino acid corresponding to serine 163 with an amino acid exhibiting a higher degree of hydrophobicity than that of the amino acid to be substituted; and
   a substitution mutation of an amino acid corresponding to asparagine 171 with an amino acid exhibiting a higher degree of hydrophobicity than that of the amino acid to be substituted.

2. The mutant decarbonylase gene according to claim 1, wherein the amino acid exhibiting a higher degree of hydrophobicity is an amino acid selected from the group consisting of phenylalanine, leucine, valine, and isoleucine.

3. The mutant decarbonylase gene according to claim 1, wherein the amino acid corresponding to glycine 90 is substituted with valine.

4. The mutant decarbonylase gene according to claim 1, wherein the amino acid corresponding to serine 163 is substituted with valine.

5. The mutant decarbonylase gene according to claim 1, wherein the amino acid corresponding to asparagine 171 is substituted with leucine.

6. A recombinant microorganism comprising the mutant decarbonylase gene according to claim 1 introduced into a host microorganism.

7. The recombinant microorganism according to claim 6, wherein the host microorganism is a bacterium of the genus *Escherichia* or *Klebsiella*.

8. A method for producing alkane comprising culturing the recombinant microorganism according to claim 6.

9. The method for producing alkane according to claim 8, which further comprises recovering alkane from a medium in which the recombinant microorganism is cultured.

10. The method for producing alkane according to claim 8, which further comprises recovering alkane from a medium in which the recombinant microorganism is cultured and purifying the recovered alkane.

11. The method for producing alkane according to claim 8, which further comprises producing alkane having 9 to 20 carbon atoms.

* * * * *

SEQUENCE LISTING

<160> NUMBER OF SEQ ID NOS: 42

<210> SEQ ID NO 1

```
<211> LENGTH: 699
<212> TYPE: DNA
<213> ORGANISM: Nostoc punctiforme PCC 73102
<220> FEATURE:
<221> NAME/KEY: CDS
<222> LOCATION: (1)..(699)

<400> SEQUENCE: 1
```

| | | | | | | | | | | | | | | | | |
|---|---|---|---|---|---|---|---|---|---|---|---|---|---|---|---|---|
| atg | cag | cag | ctt | aca | gac | caa | tct | aaa | gaa | tta | gat | ttc | aag | agc | gaa | 48 |
| Met | Gln | Gln | Leu | Thr | Asp | Gln | Ser | Lys | Glu | Leu | Asp | Phe | Lys | Ser | Glu | |
| 1 | | | | 5 | | | | | 10 | | | | | 15 | | |
| aca | tac | aaa | gat | gct | tat | agc | cgg | att | aat | gcg | atc | gtg | att | gaa | ggg | 96 |
| Thr | Tyr | Lys | Asp | Ala | Tyr | Ser | Arg | Ile | Asn | Ala | Ile | Val | Ile | Glu | Gly | |
| | | | 20 | | | | | 25 | | | | | 30 | | | |
| gaa | caa | gaa | gcc | cat | gaa | aat | tac | atc | aca | cta | gcc | caa | ctg | ctg | cca | 144 |
| Glu | Gln | Glu | Ala | His | Glu | Asn | Tyr | Ile | Thr | Leu | Ala | Gln | Leu | Leu | Pro | |
| | | 35 | | | | | 40 | | | | | 45 | | | | |
| gaa | tct | cat | gat | gaa | ttg | att | cgc | cta | tcc | aag | atg | gaa | agc | cgc | cat | 192 |
| Glu | Ser | His | Asp | Glu | Leu | Ile | Arg | Leu | Ser | Lys | Met | Glu | Ser | Arg | His | |
| | 50 | | | | | 55 | | | | | 60 | | | | | |
| aag | aaa | gga | ttt | gaa | gct | tgt | ggg | cgc | aat | tta | gct | gtt | acc | cca | gat | 240 |
| Lys | Lys | Gly | Phe | Glu | Ala | Cys | Gly | Arg | Asn | Leu | Ala | Val | Thr | Pro | Asp | |
| 65 | | | | | 70 | | | | | 75 | | | | | 80 | |
| ttg | caa | ttt | gcc | aaa | gag | ttt | ttc | tcc | ggc | cta | cac | caa | aat | ttt | caa | 288 |
| Leu | Gln | Phe | Ala | Lys | Glu | Phe | Phe | Ser | Gly | Leu | His | Gln | Asn | Phe | Gln | |
| | | | | 85 | | | | | 90 | | | | | 95 | | |
| aca | gct | gcc | gca | gaa | ggg | aaa | gtg | gtt | act | tgt | ctg | ttg | att | cag | tct | 336 |
| Thr | Ala | Ala | Ala | Glu | Gly | Lys | Val | Val | Thr | Cys | Leu | Leu | Ile | Gln | Ser | |
| | | | 100 | | | | | 105 | | | | | 110 | | | |
| tta | att | att | gaa | tgt | ttt | gcg | atc | gca | gca | tat | aac | att | tac | atc | ccc | 384 |
| Leu | Ile | Ile | Glu | Cys | Phe | Ala | Ile | Ala | Ala | Tyr | Asn | Ile | Tyr | Ile | Pro | |
| | | 115 | | | | | 120 | | | | | 125 | | | | |
| gtt | gcc | gac | gat | ttc | gcc | cgt | aaa | att | act | gaa | gga | gta | gtt | aaa | gaa | 432 |
| Val | Ala | Asp | Asp | Phe | Ala | Arg | Lys | Ile | Thr | Glu | Gly | Val | Val | Lys | Glu | |
| | 130 | | | | | 135 | | | | | 140 | | | | | |
| gaa | tac | agc | cac | ctc | aat | ttt | gga | gaa | gtt | tgg | ttg | aaa | gaa | cac | ttt | 480 |
| Glu | Tyr | Ser | His | Leu | Asn | Phe | Gly | Glu | Val | Trp | Leu | Lys | Glu | His | Phe | |
| 145 | | | | | 150 | | | | | 155 | | | | | 160 | |
| gca | gaa | tcc | aaa | gct | gaa | ctt | gaa | ctt | gca | aat | cgc | cag | aac | cta | ccc | 528 |
| Ala | Glu | Ser | Lys | Ala | Glu | Leu | Glu | Leu | Ala | Asn | Arg | Gln | Asn | Leu | Pro | |
| | | | | 165 | | | | | 170 | | | | | 175 | | |
| atc | gtc | tgg | aaa | atg | ctc | aac | caa | gta | gaa | ggt | gat | gcc | cac | aca | atg | 576 |
| Ile | Val | Trp | Lys | Met | Leu | Asn | Gln | Val | Glu | Gly | Asp | Ala | His | Thr | Met | |
| | | | 180 | | | | | 185 | | | | | 190 | | | |
| gca | atg | gaa | aaa | gat | gct | ttg | gta | gaa | gac | ttc | atg | att | cag | tat | ggt | 624 |
| Ala | Met | Glu | Lys | Asp | Ala | Leu | Val | Glu | Asp | Phe | Met | Ile | Gln | Tyr | Gly | |
| | | 195 | | | | | 200 | | | | | 205 | | | | |
| gaa | gca | ttg | agt | aac | att | ggt | ttt | tcg | act | cgc | gat | att | atg | cgc | ttg | 672 |
| Glu | Ala | Leu | Ser | Asn | Ile | Gly | Phe | Ser | Thr | Arg | Asp | Ile | Met | Arg | Leu | |
| | 210 | | | | | 215 | | | | | 220 | | | | | |
| tca | gcc | tac | gga | ctc | ata | ggt | gct | taa | | | | | | | | 699 |
| Ser | Ala | Tyr | Gly | Leu | Ile | Gly | Ala | | | | | | | | | |
| 225 | | | | 230 | | | | | | | | | | | | |

```
<210> SEQ ID NO 2
<211> LENGTH: 232
<212> TYPE: PRT
<213> ORGANISM: Nostoc punctiforme PCC 73102

<400> SEQUENCE: 2
```

| | | | | | | | | | | | | | | | |
|---|---|---|---|---|---|---|---|---|---|---|---|---|---|---|---|
| Met | Gln | Gln | Leu | Thr | Asp | Gln | Ser | Lys | Glu | Leu | Asp | Phe | Lys | Ser | Glu |
| 1 | | | | 5 | | | | | 10 | | | | | 15 | |

```
Thr Tyr Lys Asp Ala Tyr Ser Arg Ile Asn Ala Ile Val Ile Glu Gly
         20                  25                  30

Glu Gln Glu Ala His Glu Asn Tyr Ile Thr Leu Ala Gln Leu Leu Pro
             35                  40                  45

Glu Ser His Asp Glu Leu Ile Arg Leu Ser Lys Met Glu Ser Arg His
 50                  55                  60

Lys Lys Gly Phe Glu Ala Cys Gly Arg Asn Leu Ala Val Thr Pro Asp
 65                  70                  75                  80

Leu Gln Phe Ala Lys Glu Phe Phe Ser Gly Leu His Gln Asn Phe Gln
                 85                  90                  95

Thr Ala Ala Glu Gly Lys Val Val Thr Cys Leu Leu Ile Gln Ser
             100                 105                 110

Leu Ile Ile Glu Cys Phe Ala Ile Ala Ala Tyr Asn Ile Tyr Ile Pro
             115                 120                 125

Val Ala Asp Asp Phe Ala Arg Lys Ile Thr Glu Gly Val Val Lys Glu
130                 135                 140

Glu Tyr Ser His Leu Asn Phe Gly Glu Val Trp Leu Lys Glu His Phe
145                 150                 155                 160

Ala Glu Ser Lys Ala Glu Leu Glu Leu Ala Asn Arg Gln Asn Leu Pro
                165                 170                 175

Ile Val Trp Lys Met Leu Asn Gln Val Glu Gly Asp Ala His Thr Met
            180                 185                 190

Ala Met Glu Lys Asp Ala Leu Val Glu Asp Phe Met Ile Gln Tyr Gly
        195                 200                 205

Glu Ala Leu Ser Asn Ile Gly Phe Ser Thr Arg Asp Ile Met Arg Leu
210                 215                 220

Ser Ala Tyr Gly Leu Ile Gly Ala
225                 230

<210> SEQ ID NO 3
<211> LENGTH: 1026
<212> TYPE: DNA
<213> ORGANISM: Synechococcus elongatus PCC7942
<220> FEATURE:
<221> NAME/KEY: CDS
<222> LOCATION: (1)..(1026)

<400> SEQUENCE: 3 atg ttc ggt ctt atc ggt cat ctc acc agt ttg gag cag gcc cgc gac      48
Met Phe Gly Leu Ile Gly His Leu Thr Ser Leu Glu Gln Ala Arg Asp
1               5                  10                  15 gtt tct cgc agg atg ggc tac gac gaa tac gcc gat caa gga ttg gag      96
Val Ser Arg Arg Met Gly Tyr Asp Glu Tyr Ala Asp Gln Gly Leu Glu
             20                  25                  30 ttt tgg agt agc gct cct cct caa atc gtt gat gaa atc aca gtc acc     144
Phe Trp Ser Ser Ala Pro Pro Gln Ile Val Asp Glu Ile Thr Val Thr
         35                  40                  45 agt gcc aca ggc aag gtg att cac ggt cgc tac atc gaa tcg tgt ttc     192
Ser Ala Thr Gly Lys Val Ile His Gly Arg Tyr Ile Glu Ser Cys Phe
 50                  55                  60 ttg ccg gaa atg ctg gcg gcg cgc cgc ttc aaa aca gcc acg cgc aaa     240
Leu Pro Glu Met Leu Ala Ala Arg Arg Phe Lys Thr Ala Thr Arg Lys
 65                  70                  75                  80 gtt ctc aat gcc atg tcc cat gcc caa aaa cac ggc atc gac atc tcg     288
Val Leu Asn Ala Met Ser His Ala Gln Lys His Gly Ile Asp Ile Ser
                 85                  90                  95 gcc ttg ggg ggc ttt acc tcg att att ttc gag aat ttc gat ttg gcc     336
```

```
Ala Leu Gly Gly Phe Thr Ser Ile Ile Phe Glu Asn Phe Asp Leu Ala
            100                 105                 110 agt ttg cgg caa gtg cgc gac act acc ttg gag ttt gaa cgg ttc acc       384
Ser Leu Arg Gln Val Arg Asp Thr Thr Leu Glu Phe Glu Arg Phe Thr
115                 120                 125 acc ggc aat act cac acg gcc tac gta atc tgt aga cag gtg gaa gcc       432
Thr Gly Asn Thr His Thr Ala Tyr Val Ile Cys Arg Gln Val Glu Ala
        130                 135                 140 gct gct aaa acg ctg ggc atc gac att acc caa gcg aca gta gcg gtt       480
Ala Ala Lys Thr Leu Gly Ile Asp Ile Thr Gln Ala Thr Val Ala Val
145                 150                 155                 160 gtc ggc gcg act ggc gat atc ggt agc gct gtc tgc cgc tgg ctc gac       528
Val Gly Ala Thr Gly Asp Ile Gly Ser Ala Val Cys Arg Trp Leu Asp
                165                 170                 175 ctc aaa ctg ggt gtc ggt gat ttg atc ctg acg gcg cgc aat cag gag       576
Leu Lys Leu Gly Val Gly Asp Leu Ile Leu Thr Ala Arg Asn Gln Glu
            180                 185                 190 cgt ttg gat aac ctg cag gct gaa ctc ggc cgg ggc aag att ctg ccc       624
Arg Leu Asp Asn Leu Gln Ala Glu Leu Gly Arg Gly Lys Ile Leu Pro
        195                 200                 205 ttg gaa gcc gct ctg ccg gaa gct gac ttt atc gtg tgg gtc gcc agt       672
Leu Glu Ala Ala Leu Pro Glu Ala Asp Phe Ile Val Trp Val Ala Ser
210                 215                 220 atg cct cag ggc gta gtg atc gac cca gca acc ctg aag caa ccc tgc       720
Met Pro Gln Gly Val Val Ile Asp Pro Ala Thr Leu Lys Gln Pro Cys
225                 230                 235                 240 gtc cta atc gac ggg ggc tac ccc aaa aac ttg ggc agc aaa gtc caa       768
Val Leu Ile Asp Gly Gly Tyr Pro Lys Asn Leu Gly Ser Lys Val Gln
                245                 250                 255 ggt gag ggc atc tat gtc ctc aat ggc ggg gta gtt gaa cat tgc ttc       816
Gly Glu Gly Ile Tyr Val Leu Asn Gly Gly Val Val Glu His Cys Phe
            260                 265                 270 gac atc gac tgg cag atc atg tcc gct gca gag atg gcg cgg ccc gag       864
Asp Ile Asp Trp Gln Ile Met Ser Ala Ala Glu Met Ala Arg Pro Glu
        275                 280                 285 cgc cag atg ttt gcc tgc ttt gcc gag gcg atg ctc ttg gaa ttt gaa       912
Arg Gln Met Phe Ala Cys Phe Ala Glu Ala Met Leu Leu Glu Phe Glu
290                 295                 300 ggc tgg cat act aac ttc tcc tgg ggc cgc aac caa atc acg atc gag       960
Gly Trp His Thr Asn Phe Ser Trp Gly Arg Asn Gln Ile Thr Ile Glu
305                 310                 315                 320 aag atg gaa gcg atc ggt gag gca tcg gtg cgc cac ggc ttc caa ccc      1008
Lys Met Glu Ala Ile Gly Glu Ala Ser Val Arg His Gly Phe Gln Pro
                325                 330                 335 ttg gca ttg gca att tga                                              1026
Leu Ala Leu Ala Ile
            340

<210> SEQ ID NO 4
<211> LENGTH: 341
<212> TYPE: PRT
<213> ORGANISM: Synechococcus elongatus PCC7942

<400> SEQUENCE: 4

Met Phe Gly Leu Ile Gly His Leu Thr Ser Leu Glu Gln Ala Arg Asp
1               5                   10                  15

Val Ser Arg Arg Met Gly Tyr Asp Glu Tyr Ala Asp Gln Gly Leu Glu
            20                  25                  30

Phe Trp Ser Ser Ala Pro Pro Gln Ile Val Asp Glu Ile Thr Val Thr
        35                  40                  45
```

Ser Ala Thr Gly Lys Val Ile His Gly Arg Tyr Ile Glu Ser Cys Phe
        50                  55                  60

Leu Pro Glu Met Leu Ala Arg Arg Phe Lys Thr Ala Thr Arg Lys
 65                  70                  75                  80

Val Leu Asn Ala Met Ser His Ala Gln Lys His Gly Ile Asp Ile Ser
                     85                  90                  95

Ala Leu Gly Gly Phe Thr Ser Ile Ile Phe Glu Asn Phe Asp Leu Ala
                100                 105                 110

Ser Leu Arg Gln Val Arg Asp Thr Thr Leu Glu Phe Glu Arg Phe Thr
            115                 120                 125

Thr Gly Asn Thr His Thr Ala Tyr Val Ile Cys Arg Gln Val Glu Ala
            130                 135                 140

Ala Ala Lys Thr Leu Gly Ile Asp Ile Thr Gln Ala Thr Val Ala Val
145                 150                 155                 160

Val Gly Ala Thr Gly Asp Ile Gly Ser Ala Val Cys Arg Trp Leu Asp
                165                 170                 175

Leu Lys Leu Gly Val Gly Asp Leu Ile Leu Thr Ala Arg Asn Gln Glu
                180                 185                 190

Arg Leu Asp Asn Leu Gln Ala Glu Leu Gly Arg Gly Lys Ile Leu Pro
            195                 200                 205

Leu Glu Ala Ala Leu Pro Glu Ala Asp Phe Ile Val Trp Val Ala Ser
210                 215                 220

Met Pro Gln Gly Val Val Ile Asp Pro Ala Thr Leu Lys Gln Pro Cys
225                 230                 235                 240

Val Leu Ile Asp Gly Gly Tyr Pro Lys Asn Leu Gly Ser Lys Val Gln
                245                 250                 255

Gly Glu Gly Ile Tyr Val Leu Asn Gly Gly Val Val Glu His Cys Phe
                260                 265                 270

Asp Ile Asp Trp Gln Ile Met Ser Ala Ala Glu Met Ala Arg Pro Glu
            275                 280                 285

Arg Gln Met Phe Ala Cys Phe Ala Glu Ala Met Leu Leu Glu Phe Glu
            290                 295                 300

Gly Trp His Thr Asn Phe Ser Trp Gly Arg Asn Gln Ile Thr Ile Glu
305                 310                 315                 320

Lys Met Glu Ala Ile Gly Glu Ala Ser Val Arg His Gly Phe Gln Pro
                325                 330                 335

Leu Ala Leu Ala Ile
            340

<210> SEQ ID NO 5
<211> LENGTH: 40
<212> TYPE: DNA
<213> ORGANISM: Artificial
<220> FEATURE:
<223> OTHER INFORMATION: Synthetic DNA

<400> SEQUENCE: 5
cgagctcggc gcgcctgcag atgcagcagc ttacagacca                               40

<210> SEQ ID NO 6
<211> LENGTH: 40
<212> TYPE: DNA
<213> ORGANISM: Artificial
<220> FEATURE:
<223> OTHER INFORMATION: Synthetic DNA

<400> SEQUENCE: 6

```
gcaagcttgt cgacctgcag ttaagcacct atgagtccgt                    40

<210> SEQ ID NO 7
<211> LENGTH: 37
<212> TYPE: DNA
<213> ORGANISM: Artificial
<220> FEATURE:
<223> OTHER INFORMATION: Synthetic DNA

<400> SEQUENCE: 7
aaggagatat acatatgatg ttcggtctta tcggtca                       37

<210> SEQ ID NO 8
<211> LENGTH: 37
<212> TYPE: DNA
<213> ORGANISM: Artificial
<220> FEATURE:
<223> OTHER INFORMATION: Synthetic DNA

<400> SEQUENCE: 8
ttgagatctg ccatatgtca aattgccaat gccaagg                       37

<210> SEQ ID NO 9
<211> LENGTH: 31
<212> TYPE: DNA
<213> ORGANISM: Artificial
<220> FEATURE:
<223> OTHER INFORMATION: Synthetic DNA

<400> SEQUENCE: 9
aggagatata ccatgcagca gcttacagac c                             31

<210> SEQ ID NO 10
<211> LENGTH: 74
<212> TYPE: DNA
<213> ORGANISM: Artificial
<220> FEATURE:
<223> OTHER INFORMATION: Synthetic DNA

<400> SEQUENCE: 10
gctcgaattc ggatcttaca ccacatcatc ttcggcacct ggcatggcaa cgccagcacc    60
tatgagtccg tagg                                                74

<210> SEQ ID NO 11
<211> LENGTH: 37
<212> TYPE: DNA
<213> ORGANISM: Artificial
<220> FEATURE:
<223> OTHER INFORMATION: Synthetic DNA

<400> SEQUENCE: 11
aaggagatat acatatgatg ttcggtctta tcggtca                       37

<210> SEQ ID NO 12
<211> LENGTH: 37
<212> TYPE: DNA
<213> ORGANISM: Artificial
<220> FEATURE:
<223> OTHER INFORMATION: Synthetic DNA

<400> SEQUENCE: 12
ttgagatctg ccatatgtca aattgccaat gccaagg                       37

<210> SEQ ID NO 13
```

```
<211> LENGTH: 32
<212> TYPE: DNA
<213> ORGANISM: Artificial
<220> FEATURE:
<223> OTHER INFORMATION: Synthetic DNA

<400> SEQUENCE: 13
gaaaatttta tcacactagc ccaactgctg cc                                    32

<210> SEQ ID NO 14
<211> LENGTH: 36
<212> TYPE: DNA
<213> ORGANISM: Artificial
<220> FEATURE:
<223> OTHER INFORMATION: Synthetic DNA

<400> SEQUENCE: 14
tgtgataaaa ttttcatggg cttcttgttc cccttc                                36

<210> SEQ ID NO 15
<211> LENGTH: 32
<212> TYPE: DNA
<213> ORGANISM: Artificial
<220> FEATURE:
<223> OTHER INFORMATION: Synthetic DNA

<400> SEQUENCE: 15
tacatctttc tagcccaact gctgccagaa tc                                    32

<210> SEQ ID NO 16
<211> LENGTH: 38
<212> TYPE: DNA
<213> ORGANISM: Artificial
<220> FEATURE:
<223> OTHER INFORMATION: Synthetic DNA

<400> SEQUENCE: 16
ggctagaaag atgtaatttt catgggcttc ttgttccc                              38

<210> SEQ ID NO 17
<211> LENGTH: 31
<212> TYPE: DNA
<213> ORGANISM: Artificial
<220> FEATURE:
<223> OTHER INFORMATION: Synthetic DNA

<400> SEQUENCE: 17
acactagtgc aactgctgcc agaatctcat g                                     31

<210> SEQ ID NO 18
<211> LENGTH: 36
<212> TYPE: DNA
<213> ORGANISM: Artificial
<220> FEATURE:
<223> OTHER INFORMATION: Synthetic DNA

<400> SEQUENCE: 18
cagttgcact agtgtgatgt aattttcatg ggcttc                                36

<210> SEQ ID NO 19
<211> LENGTH: 33
<212> TYPE: DNA
<213> ORGANISM: Artificial
<220> FEATURE:
<223> OTHER INFORMATION: Synthetic DNA

<400> SEQUENCE: 19
```
ttctccgtgc tacaccaaaa ttttcaaaca gct                33

<210> SEQ ID NO 20
<211> LENGTH: 33
<212> TYPE: DNA
<213> ORGANISM: Artificial
<220> FEATURE:
<223> OTHER INFORMATION: Synthetic DNA

<400> SEQUENCE: 20
gtgtagcacg gagaaaaact ctttggcaaa ttg                33

<210> SEQ ID NO 21
<211> LENGTH: 40
<212> TYPE: DNA
<213> ORGANISM: Artificial
<220> FEATURE:
<223> OTHER INFORMATION: Synthetic DNA

<400> SEQUENCE: 21
ggttactgtg ctgttgattc agtctttaat tattgaatgt         40

<210> SEQ ID NO 22
<211> LENGTH: 28
<212> TYPE: DNA
<213> ORGANISM: Artificial
<220> FEATURE:
<223> OTHER INFORMATION: Synthetic DNA

<400> SEQUENCE: 22
caacagcaca gtaaccactt tcccttct                     28

<210> SEQ ID NO 23
<211> LENGTH: 29
<212> TYPE: DNA
<213> ORGANISM: Artificial
<220> FEATURE:
<223> OTHER INFORMATION: Synthetic DNA

<400> SEQUENCE: 23
gcagaagtga aagctgaact tgaacttgc                    29

<210> SEQ ID NO 24
<211> LENGTH: 32
<212> TYPE: DNA
<213> ORGANISM: Artificial
<220> FEATURE:
<223> OTHER INFORMATION: Synthetic DNA

<400> SEQUENCE: 24
agctttcact tctgcaaagt gttctttcaa cc                 32

<210> SEQ ID NO 25
<211> LENGTH: 28
<212> TYPE: DNA
<213> ORGANISM: Artificial
<220> FEATURE:
<223> OTHER INFORMATION: Synthetic DNA

<400> SEQUENCE: 25
acttgcactg cgccagaacc tacccatc                     28

<210> SEQ ID NO 26
<211> LENGTH: 28
<212> TYPE: DNA

<210> SEQ ID NO 26
<211> LENGTH: 28
<212> TYPE: DNA
<213> ORGANISM: Artificial
<220> FEATURE:
<223> OTHER INFORMATION: Synthetic DNA

<400> SEQUENCE: 26
ctggcgcagt gcaagttcaa gttcagct                                    28

<210> SEQ ID NO 27
<211> LENGTH: 33
<212> TYPE: DNA
<213> ORGANISM: Artificial
<220> FEATURE:
<223> OTHER INFORMATION: Synthetic DNA

<400> SEQUENCE: 27
cagaacgaac ccatcgtctg gaaaatgctc aac                              33

<210> SEQ ID NO 28
<211> LENGTH: 33
<212> TYPE: DNA
<213> ORGANISM: Artificial
<220> FEATURE:
<223> OTHER INFORMATION: Synthetic DNA

<400> SEQUENCE: 28
gatgggttcg ttctggcgat ttgcaagttc aag                              33

<210> SEQ ID NO 29
<211> LENGTH: 37
<212> TYPE: DNA
<213> ORGANISM: Artificial
<220> FEATURE:
<223> OTHER INFORMATION: Synthetic DNA

<400> SEQUENCE: 29
atcgtcgtga aaatgctcaa ccaagtagaa ggtgatg                          37

<210> SEQ ID NO 30
<211> LENGTH: 31
<212> TYPE: DNA
<213> ORGANISM: Artificial
<220> FEATURE:
<223> OTHER INFORMATION: Synthetic DNA

<400> SEQUENCE: 30
cattttcacg acgatgggta ggttctggcg a                                31

<210> SEQ ID NO 31
<211> LENGTH: 30
<212> TYPE: DNA
<213> ORGANISM: Artificial
<220> FEATURE:
<223> OTHER INFORMATION: Synthetic DNA

<400> SEQUENCE: 31
tggaaagtgc tcaaccaagt agaaggtgat                                  30

<210> SEQ ID NO 32
<211> LENGTH: 27
<212> TYPE: DNA
<213> ORGANISM: Artificial
<220> FEATURE:
<223> OTHER INFORMATION: Synthetic DNA

<400> SEQUENCE: 32
gttgagcact ttccagacga tgggtag                                     27

<210> SEQ ID NO 33
<211> LENGTH: 33
<212> TYPE: DNA
<213> ORGANISM: Artificial
<220> FEATURE:
<223> OTHER INFORMATION: Synthetic DNA

<400> SEQUENCE: 33
ctcaactttg tagaaggtga tgcccacaca atg             33

<210> SEQ ID NO 34
<211> LENGTH: 36
<212> TYPE: DNA
<213> ORGANISM: Artificial
<220> FEATURE:
<223> OTHER INFORMATION: Synthetic DNA

<400> SEQUENCE: 34
ttctacaaag ttgagcattt tccagacgat gggtag          36

<210> SEQ ID NO 35
<211> LENGTH: 27
<212> TYPE: DNA
<213> ORGANISM: Artificial
<220> FEATURE:
<223> OTHER INFORMATION: Synthetic DNA

<400> SEQUENCE: 35
ggtgatgtgc acacaatggc aatggaa                    27

<210> SEQ ID NO 36
<211> LENGTH: 30
<212> TYPE: DNA
<213> ORGANISM: Artificial
<220> FEATURE:
<223> OTHER INFORMATION: Synthetic DNA

<400> SEQUENCE: 36
tgtgtgcaca tcaccttcta cttggttgag                 30

<210> SEQ ID NO 37
<211> LENGTH: 31
<212> TYPE: DNA
<213> ORGANISM: Artificial
<220> FEATURE:
<223> OTHER INFORMATION: Synthetic DNA

<400> SEQUENCE: 37
attcagtttg gtgaagcatt gagtaacatt g               31

<210> SEQ ID NO 38
<211> LENGTH: 35
<212> TYPE: DNA
<213> ORGANISM: Artificial
<220> FEATURE:
<223> OTHER INFORMATION: Synthetic DNA

<400> SEQUENCE: 38
cttcaccaaa ctgaatcatg aagtcttcta ccaaa           35

<210> SEQ ID NO 39
<211> LENGTH: 39
<212> TYPE: DNA
<213> ORGANISM: Artificial
<220> FEATURE:

```
<223> OTHER INFORMATION: Synthetic DNA

<400> SEQUENCE: 39
cagtatattg aagcattgag taacattggt ttttcgact                              39

<210> SEQ ID NO 40
<211> LENGTH: 41
<212> TYPE: DNA
<213> ORGANISM: Artificial
<220> FEATURE:
<223> OTHER INFORMATION: Synthetic DNA

<400> SEQUENCE: 40
caatgcttca atatactgaa tcatgaagtc ttctaccaaa g                           41

<210> SEQ ID NO 41
<211> LENGTH: 29
<212> TYPE: DNA
<213> ORGANISM: Artificial
<220> FEATURE:
<223> OTHER INFORMATION: Synthetic DNA

<400> SEQUENCE: 41
gcattgctga acattggttt ttcgactcg                                         29

<210> SEQ ID NO 42
<211> LENGTH: 34
<212> TYPE: DNA
<213> ORGANISM: Artificial
<220> FEATURE:
<223> OTHER INFORMATION: Synthetic DNA

<400> SEQUENCE: 42
caatgttcag caatgcttca ccatactgaa tcat                                   34
```